(12) United States Patent
Nakamura et al.

(10) Patent No.: US 8,067,153 B2
(45) Date of Patent: Nov. 29, 2011

(54) GENES AND POLYPEPTIDES RELATING TO PROSTATE CANCERS

(75) Inventors: Yusuke Nakamura, Bunkyo-ku (JP);
Hidewaki Nakagawa, Bunkyo-ku (JP);
Shuichi Nakatsuru, Kawasaki (JP)

(73) Assignee: Oncotheraphy Science, Inc., Kanagawa (JP)

( * ) Notice: Subject to any disclaimer, the term of this patent is extended or adjusted under 35 U.S.C. 154(b) by 168 days.

(21) Appl. No.: 11/913,233

(22) PCT Filed: Jul. 19, 2006

(86) PCT No.: PCT/JP2006/314714
§ 371 (c)(1),
(2), (4) Date: Feb. 23, 2009

(87) PCT Pub. No.: WO2007/013479
PCT Pub. Date: Feb. 1, 2007

(65) Prior Publication Data
US 2009/0220512 A1    Sep. 3, 2009

Related U.S. Application Data

(60) Provisional application No. 60/703,107, filed on Jul. 27, 2005.

(51) Int. Cl.
*C12Q 1/00*    (2006.01)
(52) U.S. Cl. .......................................................... 435/4
(58) Field of Classification Search .................... None
See application file for complete search history.

(56) References Cited

FOREIGN PATENT DOCUMENTS

| WO | WO 02/44320 A2 * | 6/2002 |
|---|---|---|
| WO | WO 02/064761 A2 | 8/2002 |
| WO | WO 03/009814 A2 | 2/2003 |
| WO | WO 2004/031231 A2 | 4/2004 |
| WO | WO 2004/044123 A2 | 5/2004 |

OTHER PUBLICATIONS

DATABASE UniProt [Online], "*Homo sapiens* ELOVL7 protein," EBI Accession No. UNIPROT:Q589T3, whole document (May 10, 2005).
DATABASE EMBL [Online], "*Homo sapiens* ELOVL7 mRNA, complete cds," EBI Accession No. EM_HUM:AB181393, whole document (Apr. 1, 2005).
DATABASE CA [Online], "Bioinformatically detectable group of regulatory genes encoding small microRNA-like RNAs and their uses to selectively detect or inhibit gene expression," STN Database Accesion No. 141:290093, Chemical Abstracts Service, abstract (Oct. 21, 2004).
DATABASE CA [Online], "Bioinformatically detectable group of regulatory genes encoding small microRNA-like RNAs and their uses to selectively detect or inhibition gene expression," STN Database Accession No. 141:2383, Chemical Abstracts Service, abstract (Jun. 24, 2004).
Anonymous: "sIRNA Design Guidelines," [Online], URL: http://web.archive.org/web/20050724083330/http://www.ambion.com/techlib/tb/tb_506.html, whole document (Jul. 24, 2005, Retrieved on Dec. 4, 2006).
Chang, Joyce H.P. et al.; "Fatty Acid Composition and Fatty Acid Elongase and Stearoyl-CoA Desaturase Activities in Tissues of Steers Fed High Oleate Sunflower Seed"; 1992, *The Journal of Nutrition*, vol. 122, No. 11, pp. 2074-2080.
Wang, Yun et al.; "Tissue-specific, nutritional, and developmental regulation of rat fatty acid elongases"; 2005, Journal of Lipid Research, vol. 46, pp. 706-715.
Tamura et al.; "Novel Lipogenic Enzyme ELOVL7 Is Involved in Prostate Cancer Growth through Saturated Long-Chain Fatty Acid Metabolism"; *Cancer Res.*; 69(20):8133-8140 (epub Oct. 13, 2009).

* cited by examiner

*Primary Examiner* — Sean Aeder
(74) *Attorney, Agent, or Firm* — Kilpatrick Townsend & Stockton LLP

(57) ABSTRACT

The present application provides novel human gene ELOVL7 whose expression is markedly elevated in prostate cancers. The gene and polypeptide encoded by the gene can be used, for example, in the diagnosis of prostate cancers, as target molecules for developing drugs against the disease, and for attenuating cell growth of prostate cancer.

1 Claim, 5 Drawing Sheets

A

B

C

*p=0.02
**p=0.008
***p=0.003

A

B

C

GENES AND POLYPEPTIDES RELATING TO PROSTATE CANCERS

CROSS-REFERENCES TO RELATED APPLICATIONS

This application is a U.S. National Stage Application of PCT/JP2006/314714, filed Jul. 19, 2006, which claims the benefit of U.S. Provisional Application Ser. No. 60/703,107 filed Jul. 27, 2005, all of which are hereby incorporated by reference in their entirety.

TECHNICAL FIELD

The present invention relates to the field of biological science, more specifically to the field of cancer therapy and diagnosis. In particular, the present invention relates to novel polypeptides encoded by a novel gene ELOVL7 and the relationship between ELOVL7 and prostate cancer (PRC). Furthermore, the present invention relates to the ELOVL7 gene. The genes and polypeptides of the present invention can be used, for example, in the diagnosis of PRC, as target molecules for developing drugs against the disease, and for attenuating cell growth of PRC.

BACKGROUND ART

PRC is the most common malignancy in males and the second-leading cause of cancer-related death in the United States and Europe (Gronberg H. Lancet 2003; 361:859-64.), and frequency of PRC has been increasing significantly in most developed countries probably due to prevalent western-style diet and the explosion of the aging population (Gronberg H. Lancet 2003; 361:859-64., Hsing A W, Devesa S S. Epidemiol Rev 2001; 23:3-13.). Surgical and radiation therapies are effective to the localized disease, but nearly 30% of treated PRC patients still suffer from the relapse of the disease (Feldman B J, Feldman D. Nat Rev Cancer 2001; 1:34-45., Han M, et. al, J Urol 2001; 166:416-9., Isaacs W, et. al., Cancer Cell 2002; 2:113-6.). Most of the patients with relapsed or advanced disease respond well to androgen-ablation therapy because PRCs are usually androgen-dependent at a relatively early stage. However, they often acquire androgen-independent phenotype and show no or very poor response to the androgen ablation therapy. No effective anti-cancer drug or therapy is presently available to the advanced or recurrent androgen-independent PRC. Hence, development of new therapies on the basis of the molecular mechanisms of prostate carcinogenesis or hormone refractory is urgently and eagerly required.

Earlier we performed genome-wide cDNA microarray analysis of PRC cells purified from clinical cancer tissues by means of LMM (Laser Microbeam Microdissection) and identified dozens of genes whose expression levels were evidently increased in PRC cells and/or its precursor PINs, comparing with normal prostatic epithelial cells (Ashida S, et al., Cancer Res 2004; 64:5963-72.). Among the trans-activated genes, we here report characterization of a novel gene, ELOVL7 (Genebank Accession No. NM_024930, SEQ ID NO.14, encoding SEQ ID NO.15), which is very likely to play a significant role in long-chain fatty acids synthesis. ELOVL (elongation of very long chain fatty acids) family are human homologues of yeast ELOs and catalyze the elongation reaction of the long-chain fatty acids (Leonard A E, et. al., Prog Lipid Res 2004; 43: 36-54. Wang Y, et. al., J Lipid Res 2005; 46: 706-15.). The elongation system, which responsible for the addition of two carbon units to the carboxyl end of a fatty acid chain, is composed of four enzymes: a condensing enzyme (elongase, β-ketoacyl CoA synthase), β-ketoacyl CoA reductase, β-hydroxyacyl CoA dehydrase, and trans-2, 3-enoyl-CoA reductase (Leonard A E, et. al., Prog Lipid Res 2004; 43: 36-54.), and the rate of fatty acid elongation is determined by the activity of the elongase (Wang Y, et. al., J Lipid Res 2005; 46: 706-15.). Six distinct fatty acid elongase subtypes (ELOVL1-6) are reported in the mammalian so far, and each of these multiple elongation enzymes is thought to work specifically for different chain length saturated or unsaturated fatty acids (Leonard A E, et. al., Prog Lipid Res 2004; 43: 36-54., Wang Y, et. al., J Lipid Res 2005; 46: 706-15. Suneja S K, et. al., Biochim Biophys Acta. 1990; 1042: 81-5.). The metabolic pathways of long-chain fatty acids plays an important role in the maintenance of membrane lipid composition and the generation of precursors for certain cell signaling molecules, such as eicosanoids (Leonard A E, et. al., Prog Lipid Res 2004; 43: 36-54., Wang Y, et. al., J Lipid Res 2005; 46: 706-15.), thus these metabolic pathways are expected to involve some essential activity of cancer cells.

cDNA microarray technologies have provided comprehensive profiles of gene expression in normal and malignant cells, and the ability to compare the gene expression in malignant and corresponding normal cells (Okabe et al., Cancer Res 61:2129-37 (2001); Kitahara et al., Cancer Res 61: 3544-9 (2001); Lin et al., Oncogene 21:4120-8 (2002); Hasegawa et al., Cancer Res 62:7012-7 (2002)). This approach enables understanding of the complex nature of cancer cells, and helps to understand the mechanism of carcinogenesis. Identification of genes that are deregulated in tumors can lead to more precise and accurate diagnosis of individual cancers, and to develop novel therapeutic targets (Bienz and Clevers, Cell 103:311-20 (2000)). To disclose mechanisms underlying tumors from a genome-wide point of view, and to discover target molecules for diagnosis and development of novel therapeutic drugs, the present inventors have been analyzing the expression profiles of tumor cells using a cDNA microarray of 23040 genes (Okabe et al., Cancer Res 61:2129-37 (2001); Kitahara et al., Cancer Res 61:3544-9 (2001); Lin et al., Oncogene 21:4120-8 (2002); Hasegawa et al., Cancer Res 62:7012-7 (2002)).

Studies designed to reveal mechanisms of carcinogenesis have already facilitated identification of molecular targets for anti-tumor agents. For example, inhibitors of farnesyltransferase (FTIs) which were originally developed to inhibit the growth-signaling pathway related to Ras, whose activation depends on posttranslational farnesylation, has been effective in treating Ras-dependent tumors in animal models (Sun J, et. al., Oncogene 16: 1467-73 (1998)). Clinical trials on human using a combination or anti-cancer drugs and anti-HER2 monoclonal antibody, trastuzumab, have been conducted to antagonize the proto-oncogene receptor HER2/neu; and have been achieving improved clinical response and overall survival of breast-cancer patients (Molina M A, et. al., Cancer Res 61:4744-4749 (2001)). A tyrosine kinase inhibitor, STI-571, which selectively inactivates bcr-abl fusion proteins, has been developed to treat chronic myelogenous leukemias wherein constitutive activation of bcr-abl tyrosine kinase plays a crucial role in the transformation of leukocytes. Agents of these kinds are designed to suppress oncogenic activity of specific gene products (O'Dwyer M E and Druker B J, Curr Opin Oncol 12:594-7 (2000)). Therefore, gene products commonly up-regulated in cancerous cells may serve as potential targets for developing novel anti-cancer agents. In fact, novel drugs targeting abnormally expressed molecules that have causative effects on cancer growth and progression have been proven to be effective to certain types of cancers. Such drugs include Herceptin for breast cancer, Glivec (STI571) for CML and Iressa (ZD1839) for non-small cell lung cancer.

Several molecules have been known to be over-expressed in PRC and are identified as therapeutic targets or markers of PRC (Xu et al., Cancer Res 60: 6568-72 (2000); Luo et al., Cancer Res 62: 2220-6 (2002)). However, most of them are also highly expressed in other major organs. Thus, agents that target these molecules may be toxic to cancer cells but may also adversely affect normally growing cells of other organs.

It has been demonstrated that CD8+ cytotoxic T lymphocytes (CTLs) recognize epitope peptides derived from tumor-associated antigens (TAAs) presented on MHC Class I molecule, and lyse tumor cells. Since the discovery of MAGE family as the first example of TAAs, many other TAAs have been discovered using immunological approaches (Boon, Int J Cancer 54: 177-80 (1993); Boon and van der Bruggen, J Exp Med 183: 725-9 (1996); van der Bruggen et al., Science 254: 1643-7 (1991); Brichard et al., J Exp Med 178: 489-95 (1993); Kawakami et al., J Exp Med 180: 347-52 (1994)). Some of the discovered TAAs are now in the stage of clinical development as targets of immunotherapy. TAAs discovered so far include MAGE (van der Bruggen et al., Science 254: 1643-7 (1991)), gp100 (Kawakami et al., J Exp Med 180: 347-52 (1994)), SART (Shichijo et al., J Exp Med 187: 277-88 (1998)), and NY-ESO-1 (Chen et al., Proc Natl Acad Sci USA 94: 1914-8 (1997)). On the other hand, gene products which had been demonstrated to be specifically over-expressed in tumor cells, have been shown to be recognized as targets inducing cellular immune responses. Such gene products include p53 (Umano et al., Brit J Cancer 84: 1052-7 (2001)), HER2/neu (Tanaka et al., Brit J Cancer 84: 94-9 (2001)), CEA (Nukaya et al., Int J Cancer 80: 92-7 (1999)), and so on.

In spite of significant progress in basic and clinical research concerning TAAs (Rosenberg et al., Nature Med 4: 321-7 (1998); Mukherji et al., Proc Natl Acad Sci USA 92: 8078-82 (1995); Hu et al., Cancer Res 56: 2479-83 (1996)), only limited number of candidate TAAs for the treatment of adenocarcinomas, including colorectal cancer, are available. TAAs abundantly expressed in cancer cells, and at the same time which expression is restricted to cancer cells would be promising candidates as immunotherapeutic targets. Further, identification of new TAAs inducing potent and specific anti-tumor immune responses is expected to encourage clinical use of peptide vaccination strategy in various types of cancer (Boon and van der Bruggen, J Exp Med 183: 725-9 (1996); van der Bruggen et al., Science 254: 1643-7 (1991); Brichard et al., J Exp Med 178:489-95 (1993); Kawakami et al., J Exp Med 180: 347-52 (1994); Shichijo et al., J Exp Med 187: 277-88 (1998); Chen et al., Proc Natl Acad Sci USA 94: 1914-8 (1997); Harris, J Natl Cancer Inst 88: 1442-55 (1996); Butterfield et al., Cancer Res 59: 3134-42 (1999); Vissers et al., Cancer Res 59: 5554-9 (1999); van der Burg et al., J Immunol 156: 3308-14 (1996); Tanaka et al., Cancer Res 57: 4465-8 (1997); Fujie et al., Int J Cancer 80: 169-72 (1999); Kikuchi et al., Int J Cancer 81: 459-66 (1999); Oiso et al., Int J Cancer 81: 387-94 (1999)).

It has been repeatedly reported that peptide-stimulated peripheral blood mononuclear cells (PBMCs) from certain healthy donors produce significant levels of IFN-α or γ in response to the peptide, but rarely exert cytotoxicity against tumor cells in an HLA-A24 or -A0201 restricted manner in $^{51}$Cr-release assays (Kawano et al., Cancer Res 60: 3550-8 (2000); Nishizaka et al., Cancer Res 60: 4830-7 (2000); Tamura et al., Jpn J Cancer Res 92: 762-7 (2001)). However, both of HLA-A24 and HLA-A0201 are one of the common HLA alleles in Japanese, as well as Caucasian populations (Date et al., Tissue Antigens 47: 93-101 (1996); Kondo et al., J Immunol 155: 4307-12 (1995); Kubo et al., J Immunol 152: 3913-24 (1994); Imanishi et al., Proceeding of the eleventh International Histocompatibility Workshop and Conference Oxford University Press, Oxford, 1065 (1992); Williams et al., Tissue Antigen 49: 129 (1997)). Thus, antigenic peptides of cancers presented by these HLAs may be especially useful for the treatment of cancers among Japanese and Caucasian populations. Further, it is known that the induction of low-affinity CTL in vitro usually results from the use of peptide at a high concentration, generating a high level of specific peptide/MHC complexes on antigen presenting cells (APCs), which will effectively activate these CTL (Alexander-Miller et al., Proc Natl Acad Sci USA 93: 4102-7 (1996)).

SUMMARY OF THE INVENTION

To disclose the mechanism of PRC and identify novel diagnostic markers and/or drug targets for the treatment of these tumors, the present inventors analyzed the expression profiles of genes in PRC using a genome-wide cDNA microarray combined with laser microbeam microdissection. In the previous study, precise expression profiles of PRC cells (PRCs) and non-invasive precursor cells (PINs) by combining laser microdissection with genome-wide cDNA microarrays was performed. Comparing the expression profiles of invasive PRCs with normal prostatic epithelium or non-invasive precursor PINs, the present inventors identified 88 up-regulated genes and 207 down-regulated genes found in both invasive PRCs and precursor PINs. In the present invention, the present inventors focused on a novel gene, ELOVL7, which is over-expressed in PRC cells.

Immunohistochemical analysis using polyclonal anti-ELOVL7 antibody confirmed elevated expression of ELOVL7, a 281-amino-acid protein that is likely to involve elongation of long-chain fatty acids, in PRC cells comparing to that in normal prostate epithelium.

A new member of fatty acid elongase, ELOVL7 was identified as specifically over-expressed gene in PRC cells. The present inventors show that inhibition of ELOVL7 expression by siRNA resulted in drastic attenuation of PRC cell growth, demonstrating that ELOVL7 expression is essential to cell growth or viability of PRC cells. A number of epidemiological or laboratory studies have been implicated that long-chain fatty acid metabolism associated is likely to play some important roles in prostate carcinogenesis and PRC progression. By fatty-acid analysis in vivo and in vitro fatty-acid elongation assay, we validated that ELOVL7 had actual activity as a fatty acid elongase and was preferentially involved in elongation of saturated long-chain fatty acids (SLFAs) that are very abundant in animal meat diet. These findings suggest that ELOVL7 is involved in growth and survival of PRC cells probably thorough the metabolism of long-chain fatty acids and their derivatives, and that this molecule is a useful target for development of new therapeutic or preventive strategies for PRC.

ELOVL7 encodes a 281-amino acid protein. According to a Northern blot analysis, the expression of ELOVL7 was shown to be restricted to prostate, kidney and other several tissues.

The present invention provides polypeptide encoded by this gene, as well as the production and the use of the same. More specifically, the present invention provides novel human polypeptide, ELOVL7 or a functional equivalent thereof, which expressions are elevated in PRC cells.

In a preferred embodiment, the ELOVL7 polypeptide includes a 281 amino acid protein encoded by the open reading frame of SEQ ID NO: 14. The ELOVL7 polypeptide preferably includes the amino acid sequence set forth in SEQ ID NO: 15 (Genebank Accession No. NM_024930, SEQ ID NO.14, encoding SEQ ID NO.15). The present application also provides an isolated protein encoded from at least a portion of the ELOVL7 polynucleotide sequence, or polynucleotide sequences at least 80% and more preferably at least 90% identical to the sequence set forth in SEQ ID NO: 14.

The present invention further provides a novel human gene ELOVL7 whose expression is markedly elevated in a great majority of PRCs as compared to corresponding non-cancerous prostate duct epithelium. The isolated ELOVL7 gene includes a polynucleotide sequence as described in SEQ ID NO: 14. In particular, the ELOVL7 cDNA includes 3815 nucleotides that contain an open reading frame of 846 nucleotides (SEQ ID NO: 14). The present invention further encompasses polynucleotides which hybridize to and which are at least 15% and more preferably at least 25% complementary to the polynucleotide sequence set forth in SEQ ID NO: 14, to the extent that they encode a ELOVL7 protein or a functional equivalent thereof. Examples of such polynucleotides are degenerates and allelic mutants of ELOVL7 encoded by the sequence of SEQ ID NO: 14.

As used herein, an isolated gene is a polynucleotide the structure of which is not identical to that of any naturally occurring polynucleotide or to that of any fragment of a naturally occurring genomic polynucleotide spanning more than three separate genes. The term therefore includes, for example, (a) a DNA which has the sequence of part of a naturally occurring genomic DNA molecule in the genome of the organism in which it naturally occurs; (b) a polynucleotide incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion polypeptide.

Accordingly, in one aspect, the invention provides an isolated polynucleotide that encodes a polypeptide described herein or a fragment thereof. Preferably, the isolated polynucleotide includes a nucleotide sequence that is at least 60% identical to the nucleotide sequence shown in SEQ ID NO: 14. More preferably, the isolated nucleic acid molecule is at least 65%, 70%, 75%, 80%, 85%, 90%, 91%, 92%, 93%, 94%, 95%, 96%, 97%, 98%, 99% or more, identical to the nucleotide sequence shown in SEQ ID NO: 14. In the case of an isolated polynucleotide which is longer than or equivalent in length to the reference sequence, e.g., SEQ ID NO: 14, the comparison is made with the full length of the reference sequence. Where the isolated polynucleotide is shorter than the reference sequence, e.g., shorter than SEQ ID NO: 14, the comparison is made to a segment of the reference sequence of the same length (excluding any loop required by the homology calculation).

The present invention also provides a method of producing a protein by transfecting or transforming a host cell with a polynucleotide sequence encoding the ELOVL7 protein, and expressing the polynucleotide sequence. In addition, the present invention provides vectors comprising a nucleotide sequence encoding the ELOVL7 protein, and host cells harboring a polynucleotide encoding the ELOVL7 protein. Such vectors and host cells may be used for producing the ELOVL7 protein.

A binding agent that specifically recognizes the ELOVL7 protein is also provided by the present application. For example, a binding agent may be an antibody raised against a ELOVL7 protein. Alternatively, a binding agent may be a ligand specific for the protein, or a synthetic polypeptide that specifically binds the protein (see e.g., WO2004044011). An antisense polynucleotide (e.g., antisense DNA), ribozyme, and siRNA (small interfering RNA) of the ELOVL7 gene is also provided.

The present invention further provides a method for diagnosis of PRC which includes the step of determining an expression level of the gene in a biological sample from a subject, comparing the expression level of ELOVL7 gene with that in a normal sample, and defining that a high expression level of the ELOVL7 gene in the sample indicates that the subject suffers from or is at risk of developing PRC.

Further, a method of screening for a compound for treating or preventing PRC is provided by the present invention. The method includes contacting the ELOVL7 polypeptide with test compounds, and selecting test compounds that bind to or that alter the biological activity of the ELOVL7 polypeptide. In some embodiments, the screening methods can be carried by detecting the fatty acid elongation activity of ELOVL7. In these embodiments, fatty acid elongation activity can be determined using in vitro fatty acid elongation assays described herein.

The present invention further provides a method of screening for a compound for treating or preventing PRC, wherein the method includes contacting a test compound with a cell expressing the ELOVL7 polypeptide or introduced with a vector comprising the transcriptional regulatory region of ELOVL7 upstream of a reporter gene, and selecting the test compound that suppresses the expression level of the ELOVL7 polypeptide.

The present application also provides a pharmaceutical composition for treating or preventing PRC. The pharmaceutical composition may be, for example, an anti-cancer agent. The pharmaceutical composition can comprise at least a portion of antisense S-oligonucleotides, siRNA molecules or ribozymes against the ELOVL7 polynucleotide sequence shown and described in SEQ ID NO: 14, respectively. A suitable siRNA targets a sequence of SEQ ID NO: 7. Thus, an siRNA of the invention comprises a nucleotide sequence from SEQ ID NO: 7. This may be preferably selected as targets for treating or preventing PRC according to the present invention. The pharmaceutical compositions may be also those comprising the compounds selected by the present methods of screening for compounds for treating or preventing cell proliferative diseases such as PRC.

The course of action of the pharmaceutical composition is desirably to inhibit growth of the cancerous cells such as PRC cells. The pharmaceutical composition may be applied to mammals including humans and domesticated mammals.

The present invention further provides methods for treating or preventing PRC using the pharmaceutical composition provided by the present invention.

In addition, the present invention provides method for treating or preventing cancer, which method comprises the step of administering the ELOVL7 polypeptide. It is expected that anti tumor immunity is induced by the administration of the ELOVL7 polypeptide. Thus, the present invention also provides method for inducing anti tumor immunity, which method comprises the step of administering the ELOVL7 polypeptide, as well as pharmaceutical composition for treating or preventing cancer comprising the ELOVL7 polypeptide.

It is to be understood that both the foregoing summary of the invention and the following detailed description are of a preferred embodiment, and not restrictive of the invention or other alternate embodiments of the invention.

BRIEF DESCRIPTION OF THE DRAWINGS

FIG. 1(A) is photographs showing Semi-quantitative RT-PCR analysis of ELOVL7 in cancer cells (T) and normal epithelial cells (N) microdissected from 12 prostate cancer tissues. 12 horizontal lines mean clinical N/T pair cases. β2-MG was used to quantify the each of cDNA contents. FIG. 1(B) is photographs showing Multiple tissue Northern blot analysis demonstrated that ELOVL7 was expressed in the prostate, pancreas, kidney, and the length of major ELOVL7 transcript was about ~4.0 kb. P. B. leukocyte means peripheral blood leukocyte. FIG. 1(C) is photographs showing Comparison of ELOVL7 expression in PRC cells with that in normal kidney and prostate by RT-PCR, which demonstrated that ELOVL7 expression in PRC cells were obviously higher than that of normal kidney or prostate. β2-MG was used to quantify the each of cDNA contents.

FIG. 3(A) is photographs showing Knockdown effect of siRNA on ELOVL7 in LNCaP prostate cell line. Semi-quantitative RT-PCR was performed using cells transfected with siRNA-expressing vectors to ELOVL7 (si#5) as well as a negative control vector (siEGFP). β2-MG was used to quantify RNAs. FIG. 3(B) is photographs showing Colony formation assay of LNCaP cells transfected with indicated siRNA-expressing vectors to ELOVL7 (si#5) and a negative control vector (siEGFP). Cells were visualized with 0.1% crystal violet staining after 14-day incubation with Geneticin. FIG. 3(C) is a bar chart showing MTT assay of each of LNCaP cells transfected with indicated siRNA-expressing vectors to ELOVL7 (si#5) and a negative control vector (siEGFP). Each average is plotted with error bars indicating SD (standard deviation) after 14-day incubation with Geneticin. ABS on Y-axis means absorbance at 490 nm, and at 630 nm as reference, measured with a microplate reader. These experiments were carried out in triplicate.  Means p value of <0.01 (Students' t-test). FIG. 3(D) Knockdown effect of siRNA on ELOVL7 in 22Rv1 prostate cell line. Semi-quantitative RT-PCR was performed using cells transfected with siRNA-expressing vectors to ELOVL7 (si#5) as well as a negative control vector (siEGFP). β2-MG was used to quantify RNAs. FIG. 3(E) Colony formation assay of 22Rv1 cells transfected with indicated siRNA-expressing vectors to ELOVL7 (si#5) and a negative control vector (siEGFP). Cells were visualized with 0.1% crystal violet staining after 14-day incubation with Geneticin. FIG. 3(F) MTT assay of each of 22Rv1 cells transfected with indicated siRNA-expressing vectors to ELOVL7 (si#5) and a negative control vector (siEGFP). Each average is plotted with error bars indicating SD (standard deviation) after 14-day incubation with Geneticin. ABS on Y-axis means absorbance at 490 nm, and at 630 nm as reference, measured with a microplate reader. These experiments were carried out in triplicate.  Means p value of <0.01 (Students' t-test).

DETAILED DESCRIPTION OF THE INVENTION

Figure 1:
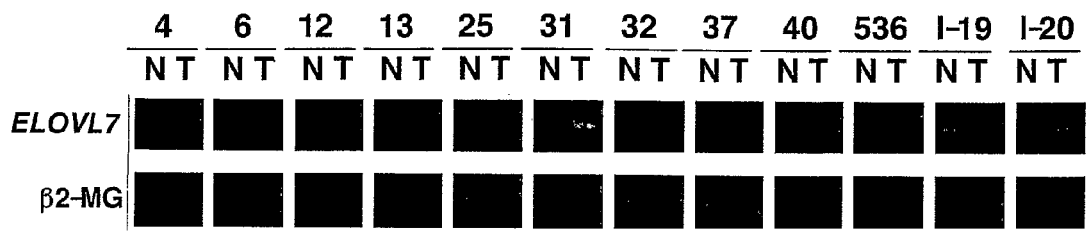
FIG. 1 shows ELOVL7 mRNA expression level in PRC cells and tissue distribution of ELOVL7 mRNA.
Figure 1:
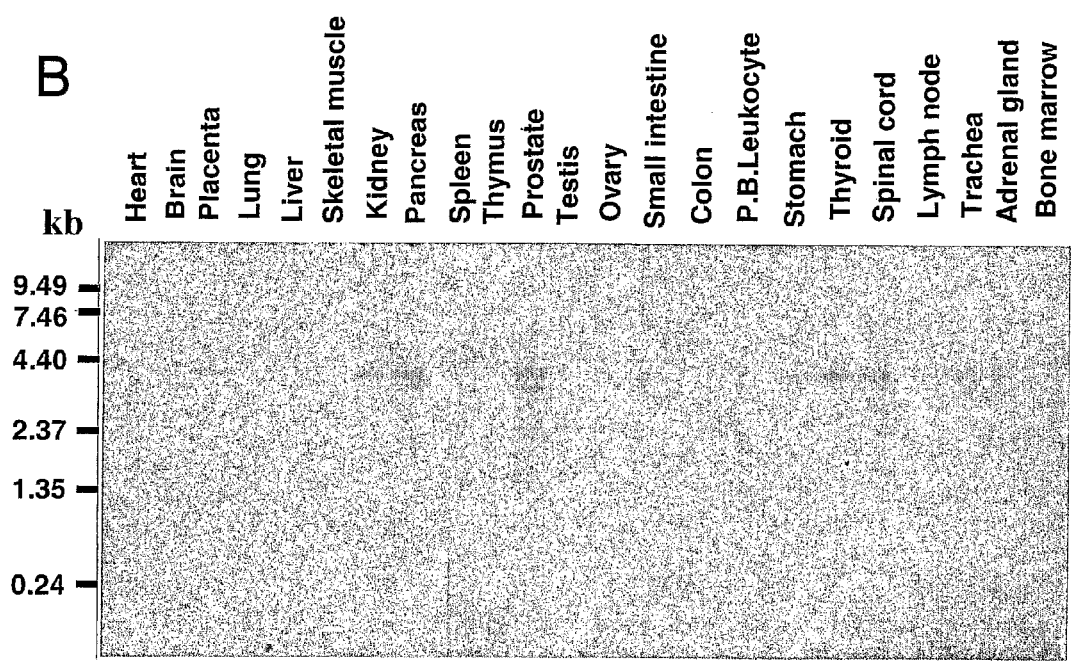
Figure 1:
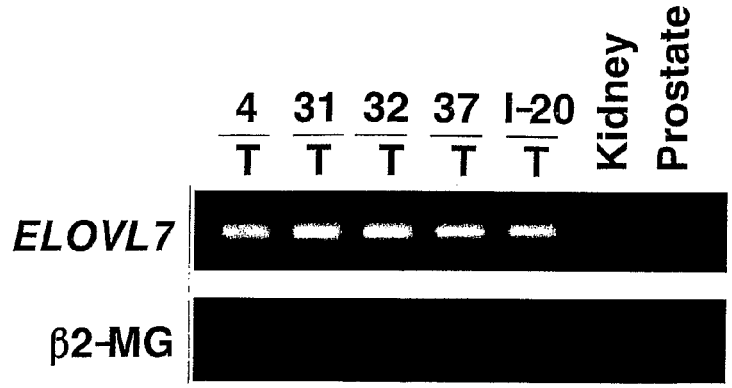

The words "a", "an" and "the" as used herein mean "at least one" unless otherwise specifically indicated.

To disclose the mechanism of PRC and identify novel diagnostic markers and/or drug targets for the treatment and/or prevention of these tumors, the present inventors analyzed the expression profiles of genes in PRC using a genome-wide cDNA microarray combined with laser microbeam microdissection. As a result, ELOVL7 specifically over-expressed in PRC cells was identified. Furthermore, suppression of the expression of ELOVL7 gene with small interfering RNAs (siRNAs) resulted in a significant growth-inhibition of cancerous cells. These findings suggest that ELOVL7 render oncogenic activities to cancer cells, and that inhibition of the activity of these proteins could be a promising strategy for the treatment and prevention of proliferative diseases such as PRC.

ELOVL7

The present application identifies novel human gene ELOVL7 whose expression is markedly elevated in PRC cells compared to that in normal prostate epithelium. The ELOVL7 cDNA consists of 3815 nucleotides that contain an open reading frame of 846 nucleotides as set forth in SEQ ID NO: 14. The open reading frame encodes a putative 281-amino acid protein.

Thus, the present invention provides substantially pure polypeptides encoded by this gene including a polypeptide comprising the amino acid sequence of SEQ ID NO: 15, as well as functional equivalents thereof, to the extent that they encode a ELOVL7 protein. Examples of polypeptides functionally equivalent to SEQ ID NO: 15 include, for example, homologous proteins of other organisms corresponding to the human ELOVL7 protein, as well as mutants of human ELOVL7 proteins.

In the present invention, the term "functionally equivalent" means that the subject polypeptide has fatty acid elongation activity, or has the activity to promote cell proliferation like the ELOVL7 protein and to confer oncogenic activity to cancer cells. Whether the subject polypeptide has a cell proliferation activity or not can be judged by introducing the DNA encoding the subject polypeptide into a cell, expressing the respective polypeptide and detecting promotion of proliferation of the cells or increase in colony forming activity. Such cells include, for example, NIH3T3, COS7 and HEK293.

A convenient means for detecting functionally equivalent polypeptides is to measure fatty acid elongation activity of the polypeptide. Thus, for example, variant polypeptides (e.g., polypeptides having at least about 80% sequence identity to SEQ ID NO: 15 or polypeptides encoded by polynucleotides that hybridize under stringent conditions to SEQ ID NO: 14) can be tested to determine fatty acid elongation activity. Methods for detecting fatty acid elongation activity are disclosed below. Typically, the methods involve contacting a test polypeptide appropriate reagents for carrying out the assay. Such reagents may include, for example, a fatty acid substrate (e.g., Arachidoyl-CoA), Malonyl-CoA, NADPH, and a reagent for detecting the elongation product. The methods further comprise detecting the level of fatty acid elongation of the fatty acid substrate and measuring the fatty acid elongation activity by correlating the fatty acid elongation level with the fatty acid elongation activity.

Methods for preparing polypeptides functionally equivalent to a given protein are well known by a person skilled in the art and include known methods of introducing mutations into the protein. For example, one skilled in the art can prepare polypeptides functionally equivalent to the human ELOVL7 protein by introducing an appropriate mutation in the amino acid sequence of these proteins by site-directed mutagenesis (Hashimoto-Gotoh et al., Gene 152:271-5 (1995); Zoller and Smith, Methods Enzymol 100: 468-500 (1983); Kramer et al., Nucleic Acids Res. 12:9441-9456 (1984); Kramer and Fritz, Methods Enzymol 154: 350-67 (1987); Kunkel, Proc Natl Acad Sci USA 82: 488-92 (1985); Kunkel, Methods Enzymol 85: 2763-6 (1988)). Amino acid mutations can occur in nature, too. The polypeptide of the present invention includes those proteins having the amino acid sequences of the human ELOVL7 protein in which one or more amino acids are mutated, provided the resulting mutated polypeptides are functionally equivalent to the human ELOVL7 protein. The number of amino acids to be mutated in such a mutant is generally 10 amino acids or less, preferably 6 amino acids or less, and more preferably 3 amino acids or less.

Mutated or modified proteins, proteins having amino acid sequences modified by substituting, deleting, inserting and/or adding one or more amino acid residues of a certain amino acid sequence, have been known to retain the original biological activity (Mark et al., Proc Natl Acad Sci USA 81: 5662-6 (1984); Zoller and Smith, Nucleic Acids Res 10:6487-500 (1982); Dalbadie-McFarland et al., Proc Natl Acad Sci USA 79: 6409-13 (1982)).

The amino acid residue to be mutated is preferably mutated into a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

An example of a polypeptide to which one or more amino acids residues are added to the amino acid sequence of human ELOVL7 protein is a fusion protein containing the human ELOVL7 protein. Fusion proteins, fusions of the human ELOVL7 protein and other peptides or proteins, are included in the present invention. Fusion proteins can be made by techniques well known to a person skilled in the art, such as by linking the DNA encoding the human ELOVL7 protein of the invention with DNA encoding other peptides or proteins, so that the frames match, inserting the fusion DNA into an expression vector and expressing it in a host. There is no restriction as to the peptides or proteins fused to the protein of the present invention.

Known peptides that can be used as peptides that are fused to the protein of the present invention include, for example, FLAG (Hopp et al., Biotechnology 6: 1204-10 (1988)), 6×His containing six H is (histidine) residues, 10×His, Influenza agglutinin (HA), human c-myc fragment, VSP-GP fragment, p18HIV fragment, T7-tag, HSV-tag, E-tag, SV40T antigen fragment, lck tag, α-tubulin fragment, B-tag, Protein C fragment and the like. Examples of proteins that may be fused to a protein of the invention include GST (glutathione-S-transferase), Influenza agglutinin (HA), immunoglobulin constant region, β-galactosidase, MBP (maltose-binding protein) and such.

Fusion proteins can be prepared by fusing commercially available DNA, encoding the fusion peptides or proteins discussed above, with the DNA encoding the polypeptide of the present invention and expressing the fused DNA prepared.

An alternative method known in the art to isolate functionally equivalent polypeptides is, for example, the method using a hybridization technique (Sambrook et al., Molecular Cloning 2nd ed. 9.47-9.58, Cold Spring Harbor Lab. Press (1989)). One skilled in the art can readily isolate a DNA having high homology with a whole or part of the DNA sequence encoding the human ELOVL7 protein (i.e., SEQ ID NO: 14), and isolate functionally equivalent polypeptides to the human ELOVL7 protein from the isolated DNA. The polypeptides of the present invention include those that are encoded by DNA that hybridize with a whole or part of the DNA sequence encoding the human ELOVL7 protein and are functionally equivalent to the human ELOVL7 protein. These polypeptides include mammal homologues corresponding to the protein derived from human (for example, a polypeptide encoded by a monkey, rat, rabbit and bovine gene). In isolating a cDNA highly homologous to the DNA encoding the human ELOVL7 protein from animals, it is particularly preferable to use tissues from prostate.

The condition of hybridization for isolating a DNA encoding a polypeptide functionally equivalent to the human ELOVL7 protein can be routinely selected by a person skilled in the art. For example, hybridization may be performed by conducting prehybridization at 68° C. for 30 min or longer using "Rapid-hyb buffer" (Amersham LIFE SCIENCE), adding a labeled probe, and warming at 68° C. for 1 hour or longer. The following washing step can be conducted, for example, in a low stringent condition. A low stringent condition is, for example, 42° C., 2×SSC, 0.1% SDS, or preferably 50° C., 2×SSC, 0.1% SDS. More preferably, high stringent conditions are used. A high stringent condition is, for example, washing 3 times in 2×SSC, 0.01% SDS at room temperature for 20 min, then washing 3 times in 1×SSC, 0.1% SDS at 37° C. for 20 min, and washing twice in 1×SSC, 0.1% SDS at 50° C. for 20 min. However, several factors, such as temperature and salt concentration, can influence the stringency of hybridization and one skilled in the art can suitably select the factors to achieve the requisite stringency.

In place of hybridization, a gene amplification method, for example, the polymerase chain reaction (PCR) method, can be utilized to isolate a DNA encoding a polypeptide functionally equivalent to the human ELOVL7 protein, using a primer synthesized based on the sequence information of the protein encoding DNA (SEQ ID NO: 14).

Polypeptides that are functionally equivalent to the human ELOVL7 protein encoded by the DNA isolated through the above hybridization techniques or gene amplification techniques normally have a high homology to the amino acid sequence of the human ELOVL7 protein. "High homology" typically refers to a homology of 40% or higher, preferably 60% or higher, more preferably 80% or higher, even more preferably 85%, 90%, 93%, 95%, 98%, 99% or higher between a polypeptide sequence or a polynucleotide sequence and a reference sequence. Percent homologies (also referred to as percent identity) are typically carried out between two optimally aligned sequences. Methods of alignment of sequences for comparison are well-known in the art. Optimal alignment of sequences and comparison can be conducted, e.g., using the algorithm in "Wilbur and Lipman, Proc Natl Acad Sci USA 80: 726-30 (1983)".

A polypeptide of the present invention have variations in amino acid sequence, molecular weight, isoelectric point, the presence or absence of sugar chains, or form, depending on the cell or host used to produce it or the purification method utilized. Nevertheless, so long as it has a function equivalent to that of the human ELOVL7 protein of the present invention, it is within the scope of the present invention.

The polypeptides of the present invention can be prepared as recombinant proteins or natural proteins, by methods well known to those skilled in the art. A recombinant protein can be prepared by inserting a DNA, which encodes the polypeptide of the present invention (for example, the DNA comprising the nucleotide sequence of SEQ ID NO: 14), into an appropriate expression vector, introducing the vector into an appropriate host cell, obtaining the extract, and purifying the polypeptide by subjecting the extract to chromatography, e.g., ion exchange chromatography, reverse phase chromatography, gel filtration or affinity chromatography utilizing a column to which antibodies against the protein of the present invention is fixed or by combining more than one of aforementioned columns.

Also when the polypeptide of the present invention is expressed within host cells (for example, animal cells and *E. coli*) as a fusion protein with glutathione-S-transferase protein or as a recombinant protein supplemented with multiple histidines, the expressed recombinant protein can be purified using a glutathione column or nickel column. Alternatively, when the polypeptide of the present invention is expressed as a protein tagged with c-myc, multiple histidines or FLAG, it can be detected and purified using antibodies to c-myc, H is or FLAG, respectively.

After purifying the fusion protein, it is also possible to exclude regions other than the objective polypeptide by cutting with thrombin or factor-Xa as required.

A natural protein can be isolated by methods known to a person skilled in the art, for example, by contacting the affinity column, in which antibodies binding to the ELOVL7 protein described below are bound, with the extract of tissues or cells expressing the polypeptide of the present invention. The antibodies can be polyclonal antibodies or monoclonal antibodies.

The present invention also encompasses partial peptides of the polypeptide of the present invention. The partial peptide has an amino acid sequence specific to the polypeptide of the present invention and consists of at least 7 amino acids, preferably 8 amino acids or more, and more preferably 9 amino acids or more. The partial peptide can be used, for example, for preparing antibodies against the polypeptide of the present invention, screening for a compound that binds to the polypeptide of the present invention, and screening for inhibitors of the polypeptide of the present invention.

A partial peptide of the invention can be produced by genetic engineering, by known methods of peptide synthesis or by digesting the polypeptide of the invention with an appropriate peptidase. For peptide synthesis, for example, solid phase synthesis or liquid phase synthesis may be used.

The present invention further provides polynucleotides that encode such ELOVL7 polypeptides described above. The polynucleotides of the present invention can be used for the in vivo or in vitro production of the polypeptide of the present invention as described above, or can be applied to gene therapy for diseases attributed to genetic abnormality in the gene encoding the protein of the present invention. Any form of the polynucleotide of the present invention can be used so long as it encodes the polypeptide of the present invention, including mRNA, RNA, cDNA, genomic DNA, chemically synthesized polynucleotides. The polynucleotide of the present invention includes a DNA comprising a given nucleotide sequences as well as its degenerate sequences, so long as the resulting DNA encodes a polypeptide of the present invention.

The polynucleotide of the present invention can be prepared by methods known to a person skilled in the art. For example, the polynucleotide of the present invention can be prepared by: preparing a cDNA library from cells which express the polypeptide of the present invention, and conducting hybridization using a partial sequence of the DNA of the present invention (for example, SEQ ID NO: 14) as a probe. A cDNA library can be prepared, for example, by the method described in Sambrook et al., Molecular Cloning, Cold Spring Harbor Laboratory Press (1989); alternatively, commercially available cDNA libraries may be used. A cDNA library can be also prepared by: extracting RNAs from cells expressing the polypeptide of the present invention, synthesizing oligo DNAs based on the sequence of the DNA of the present invention (for example, SEQ ID NO: 14), conducting PCR using the oligo DNAs as primers, and amplifying cDNAs encoding the protein of the present invention.

In addition, by sequencing the nucleotides of the obtained cDNA, the translation region encoded by the cDNA can be routinely determined, and the amino acid sequence of the polypeptide of the present invention can be easily obtained.

Moreover, by screening the genomic DNA library using the obtained cDNA or parts thereof as a probe, the genomic DNA can be isolated.

More specifically, mRNAs may first be prepared from a cell, tissue or organ (e.g., prostate) in which the object polypeptide of the invention is expressed. Known methods can be used to isolate mRNAs; for instance, total RNA may be prepared by guanidine ultracentrifugation (Chirgwin et al., Biochemistry 18:5294-9 (1979)) or AGPC method (Chomczynski and Sacchi, Anal Biochem 162:156-9 (1987)). In addition, mRNA may be purified from total RNA using mRNA Purification Kit (Pharmacia) and such. Alternatively, mRNA may be directly purified by QuickPrep mRNA Purification Kit (Pharmacia).

The obtained mRNA is used to synthesize cDNA using reverse transcriptase. cDNA may be synthesized using a commercially available kit, such as the AMV Reverse Transcriptase First-strand cDNA Synthesis Kit (Seikagaku Kogyo). Alternatively, cDNA may be synthesized and amplified following the 5'-RACE method (Frohman et al., Proc Natl Acad Sci USA 85: 8998-9002 (1988); Belyavsky et al., Nucleic Acids Res 17: 2919-32 (1989)), which uses a primer and such, described herein, the 5'-Ampli FINDER RACE Kit (Clontech), and polymerase chain reaction (PCR).

A desired DNA fragment is prepared from the PCR products and ligated with a vector DNA. The recombinant vectors are used to transform *E. coli* and such, and a desired recombinant vector is prepared from a selected colony. The nucleotide sequence of the desired DNA can be verified by conventional methods, such as dideoxynucleotide chain termination.

The nucleotide sequence of a polynucleotide of the invention may be designed to be expressed more efficiently by taking into account the frequency of codon usage in the host to be used for expression (Grantham et al., Nucleic Acids Res 9: 43-74 (1981)). The sequence of the polynucleotide of the present invention may be altered by a commercially available kit or a conventional method. For instance, the sequence may be altered by digestion with restriction enzymes, insertion of a synthetic oligonucleotide or an appropriate polynucleotide fragment, addition of a linker, or insertion of the initiation codon (ATG) and/or the stop codon (TAA, TGA or TAG).

Specifically, the polynucleotide of the present invention encompasses the DNA comprising the nucleotide sequence of SEQ ID NO: 14.

Furthermore, the present invention provides a polynucleotide that hybridizes under stringent conditions with a polynucleotide having a nucleotide sequence of SEQ ID NO: 14, and encodes a polypeptide functionally equivalent to the ELOVL7 protein of the invention described above. One skilled in the art may appropriately choose stringent conditions. For example, low stringent condition can be used. More preferably, high stringent condition can be used. These conditions are the same as that described above. The hybridizing DNA above is preferably a cDNA or a chromosomal DNA.

The present invention also provides a polynucleotide which is complementary to the polynucleotide encoding human ELOVL7 protein (SEQ ID NO: 14) or the complementary strand thereof, and which comprises at least 15 nucleotides. The polynucleotide of the present invention is preferably a polynucleotide which specifically hybridizes with the DNA encoding the ELOVL7 polypeptide of the present invention. The term "specifically hybridize" as used herein, means that cross-hybridization does not occur significantly with DNA encoding other proteins, under the usual hybridizing conditions, preferably under stringent hybridizing conditions. Such polynucleotides include, probes, primers, nucleotides and nucleotide derivatives (for example, antisense oligonucleotides and ribozymes), which specifically hybridize with DNA encoding the polypeptide of the invention or its complementary strand. Moreover, such polynucleotide can be utilized for the preparation of DNA chip.

Vectors and Host Cells

The present invention also provides a vector and host cell into which a polynucleotide of the present invention is introduced. A vector of the present invention is useful to keep a polynucleotide, especially a DNA, of the present invention in host cell, to express the polypeptide of the present invention, or to administer the polynucleotide of the present invention for gene therapy.

When *E. coli* is a host cell and the vector is amplified and produced in a large amount in *E. coli* (e.g., JM109, DH5α, HB101 or XL1Blue), the vector should have "ori" to be amplified in *E. coli* and a marker gene for selecting transformed *E. coli* (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc. can be used. In addition, pGEM-T, pDIRECT and pT7 can also be used for subcloning and extracting cDNA as well as the vectors described above. When a vector is used to produce the protein of the present invention, an expression vector is especially useful. For example, an expression vector to be expressed in *E. coli* should have the above characteristics to be amplified in *E. coli*. When *E. coli*, such as JM109, DH5α, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in *E. coli*. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for polypeptide secretion. An exemplary signal sequence that directs the polypeptide to be secreted to the periplasm of the *E. coli* is the pelB signal sequence (Lei et al., J Bacteriol 169: 4379 (1987)). Means for introducing of the vectors into the target host cells include, for example, the calcium chloride method, and the electroporation method.

In addition to *E. coli*, for example, expression vectors derived from mammals (for example, pcDNA3 (Invitrogen) and pEGF-BOS (Mizushima and Nagata, Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "*Pichia* Expression Kit" (Invitrogen), pNV11, SP-Q01) and expression vectors derived from *Bacillus subtilis* (e.g., pPL608, pKTH50) can be used for producing the polypeptide of the present invention.

In order to express the vector in animal cells, such as CHO, COS or NIH3T3 cells, the vector should have a promoter necessary for expression in such cells, for example, the SV40 promoter (Mulligan et al., Nature 277: 108 (1979)), the MMLV-LTR promoter, the EF1α promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

Producing Polypeptides

In addition, the present invention provides methods for producing a polypeptide of the present invention. The polypeptides may be prepared by culturing a host cell which harbors an expression vector comprising a gene encoding the polypeptide. According to needs, methods may be used to express a gene stably and, at the same time, to amplify the copy number of the gene in cells. For example, a vector comprising the complementary DHFR gene (e.g., pCHO I) may be introduced into CHO cells in which the nucleic acid synthesizing pathway is deleted, and then amplified by methotrexate (MTX). Furthermore, in case of transient expression of a gene, the method wherein a vector comprising a replication origin of SV40 (pcD, etc.) is transformed into COS cells comprising the SV40 T antigen expressing gene on the chromosome can be used.

A polypeptide of the present invention obtained as above may be isolated from inside or outside (such as medium) of host cells and purified as a substantially pure homogeneous polypeptide. The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example by column chromatography, polyacrylamide gel electrophoresis, or HPLC analysis. The method for polypeptide isolation and purification is not limited to any specific method; in fact, any standard method may be used.

For instance, column chromatography, filter, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the polypeptide.

Examples of chromatography include, for example, affinity chromatography, ion-exchange chromatography, hydrophobic chromatography, gel filtration, reverse phase chromatography, adsorption chromatography, and such (Strategies for Protein Purification and Characterization: A Laboratory Course Manual. Ed. Daniel R. Marshak et al., Cold Spring Harbor Laboratory Press (1996)). These chromatographies may be performed by liquid chromatography, such as HPLC and FPLC. Thus, the present invention provides for highly purified polypeptides prepared by the above methods.

A polypeptide of the present invention may be optionally modified or partially deleted by treating it with an appropriate protein modification enzyme before or after purification. Useful protein modification enzymes include, but are not limited to, trypsin, chymotrypsin, lysylendopeptidase, protein kinase, glucosidase and so on.

Antibodies

The present invention provides an antibody that binds to the polypeptide of the invention. The antibody of the invention can be used in any form, such as monoclonal or polyclonal antibodies, and includes antiserum obtained by immunizing an animal such as a rabbit with the polypeptide of the invention, all classes of polyclonal and monoclonal antibodies, human antibodies and humanized antibodies produced by genetic recombination.

A polypeptide of the invention used as an antigen to obtain an antibody may be derived from any animal species, but preferably is derived from a mammal such as a human, mouse, or rat, more preferably from a human. A human-derived polypeptide may be obtained from the nucleotide or amino acid sequences disclosed herein.

According to the present invention, the polypeptide to be used as an immunization antigen may be a complete protein or a partial peptide of the protein. A partial peptide may comprise, for example, the amino (N)-terminal or carboxy (C)-terminal fragment of a polypeptide of the present invention.

Herein, an antibody is defined as a protein that reacts with either the full length or a fragment of a polypeptide of the present invention.

A gene encoding a polypeptide of the invention or its fragment may be inserted into a known expression vector, which is then used to transform a host cell as described herein. The desired polypeptide or its fragment may be recovered from the outside or inside of host cells by any standard method, and may subsequently be used as an antigen. Alternatively, whole cells expressing the polypeptide or their lysates or a chemically synthesized polypeptide may be used as the antigen.

Any mammalian animal may be immunized with the antigen, but preferably the compatibility with parental cells used for cell fusion is taken into account. In general, animals of Rodentia, Lagomorpha or Primates are used. Animals of Rodentia include, for example, mouse, rat and hamster. Animals of Lagomorpha include, for example, rabbit. Animals of Primates include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum is examined by a standard method for an increase in the amount of desired antibodies.

Polyclonal antibodies against the polypeptides of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the polypeptide of the present invention using, for example, an affinity column coupled with the polypeptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

In addition to the above method, in which a non-human animal is immunized with an antigen for preparing hybridoma, human lymphocytes such as those infected by EB virus may be immunized with a polypeptide, polypeptide expressing cells or their lysates in vitro. Then, the immunized lymphocytes are fused with human-derived myeloma cells that are capable of indefinitely dividing, such as U266, to yield a hybridoma producing a desired human antibody that is able to bind to the polypeptide can be obtained (Unexamined Published Japanese Patent Application No. (JP-A) Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography or an affinity column to which the polypeptide of the present invention is coupled. The antibody of the present invention can be used not only for purification and detection of the polypeptide of the present invention, but also as a candidate for antagonists of the polypeptide of the present invention. In addition, this antibody can be applied to the antibody treatment for diseases related to the polypeptide of the present invention. When the obtained antibody is to be administered to the human body (antibody treatment), a human antibody or a humanized antibody is preferable for reducing immunogenicity.

For example, transgenic animals having a repertory of human antibody genes may be immunized with an antigen selected from a polypeptide, polypeptide expressing cells or their lysates. Antibody producing cells are then collected from the animals and fused with myeloma cells to obtain hybridoma, from which human antibodies against the polypeptide can be prepared (see WO92-03918, WO93-2227, WO94-02602, WO94-25585, WO96-33735 and WO96-34096).

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal, Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the polypeptides of the invention. For instance, the antibody fragment may be Fab, F(ab')$_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, comprising the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see e.g. Verhoeyen et al., *Science* 239: 1534-1536 (1988)). Accordingly, such humanized antibodies are chimeric antibodies, wherein substantially less than an intact human variable domain has been substituted by the corresponding sequence from a non-human species.

Fully human antibodies comprising human variable regions in addition to human framework and constant regions can also be used. Such antibodies can be produced using various techniques known in the art. For example in vitro methods involve use of recombinant libraries of human antibody fragments displayed on bacteriophage (e.g., Hoogenboom & Winter, J. Mol. Biol. 227:381 (1992), Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F.F. (Pharmacia).

Exemplary chromatography, with the exception of affinity includes, for example, ion-exchange chromatography, hydrophobic chromatography, gel filtration, reverse-phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a polypeptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the polypeptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of the polypeptide of the invention, by exposing the antibody of the invention to a sample assumed to contain the polypeptide of the invention, and detecting or measuring the immune complex formed by the antibody and the polypeptide.

Because the method of detection or measurement of the polypeptide according to the invention can specifically detect or measure a polypeptide, the method may be useful in a variety of experiments in which the polypeptide is used.

Antisense Polynucleotides, Small Interfering RNAs and Ribozymes

The present invention includes an antisense oligonucleotide that hybridizes with any site within the nucleotide sequence of SEQ ID NO: 14. This antisense oligonucleotide is preferably against at least about 15 continuous nucleotides of the nucleotide sequence of SEQ ID NO: 14. The above-mentioned antisense oligonucleotide, which contains an initiation codon in the above-mentioned at least 15 continuous nucleotides, is even more preferred.

Derivatives or modified products of antisense oligonucleotides can also be used as antisense oligonucleotides. Examples of such modified products include lower alkyl phosphonate modifications such as methyl-phosphonate-type or ethyl-phosphonate-type, phosphorothioate modifications and phosphoroamidate modifications.

The term "antisense oligonucleotides" as used herein means, not only those in which the nucleotides corresponding to those constituting a specified region of a DNA or mRNA are entirely complementary, but also those having a mismatch of one or more nucleotides, as long as the DNA or mRNA and the antisense oligonucleotide can specifically hybridize with the nucleotide sequence of SEQ ID NO: 14.

Such polynucleotides are contained as those having, in the "at least about 15 continuous nucleotide sequence region", a homology of at least 70% or higher, preferably at 80% or higher, more preferably about 90% or higher, even more preferably about 95% or higher. The algorithm stated herein can be used to determine the homology. Algorithms known in the art can be used to determine the homology. Furthermore, derivatives or modified products of the antisense-oligonucleotides can also be used as antisense-oligonucleotides in the present invention. Examples of such modified products include lower alkyl phosphonate modifications such as methyl-phosphonate-type or ethyl-phosphonate-type, phosphorothioate modifications and phosphoroamidate modifications.

Such antisense polynucleotides are useful as probes for the isolation or detection of DNA encoding the polypeptide of the invention or as a primer used for amplifications.

The antisense oligonucleotide derivatives of the present invention act upon cells producing the polypeptide of the invention by binding to the DNA or mRNA encoding the polypeptide, inhibiting its transcription or translation, promoting the degradation of the mRNA and inhibiting the expression of the polypeptide of the invention, thereby resulting in the inhibition of the polypeptide's function.

The present invention also includes small interfering RNAs (siRNA) comprising a combination of a sense strand nucleic acid and an antisense strand nucleic acid of the nucleotide sequence of SEQ ID NO: 14. More specifically, such siRNA for suppressing the expression of ELOVL7 include those that target the nucleotide sequence of SEQ ID NO: 7.

The term "siRNA" refers to a double stranded RNA molecule which prevents translation of a target mRNA. Standard techniques are used for introducing siRNA into cells, including those wherein DNA is used as the template to transcribe RNA. The siRNA comprises a sense nucleic acid sequence and an antisense nucleic acid sequence of the polynucleotide encoding human ELOVL7 protein (SEQ ID NO: 14). The siRNA is constructed such that a single transcript (double stranded RNA) has both the sense and complementary antisense sequences from the target gene, e.g., a hairpin.

Binding of the siRNA to a transcript corresponding to ELOVL7 in the target cell results in a reduction in the protein production by the cell. The length of the oligonucleotide is at least 10 nucleotides and may be as long as the naturally-occurring the transcript. Preferably, the oligonucleotide is less than about 75, about 50, about 25 nucleotides in length. Most preferably, the oligonucleotide is about 19 to about 25 nucleotides in length. Examples of ELOVL7 siRNA oligonucleotide which inhibit the growth of the cancer cell include the target sequence containing SEQ ID NO: 7. Furthermore, in order to enhance the inhibition activity of the siRNA, nucleotide "u" can be added to 3'end of the antisense strand of the target sequence. The number of "u"s to be added is at least about 2, generally about 2 to about 10, preferably about 2 to about 5. The added "u"s form single strand at the 3' end of the antisense strand of the siRNA.

An ELOVL7 siRNA is directly introduced into the cells in a form that is capable of binding to the mRNA transcripts. In these embodiments, the siRNA molecules of the invention are typically modified as described above for antisense molecules. Other modifications are also possible, for example, cholesterol-conjugated siRNAs have shown improved pharmacological properties (Song et al. *Nature Med.* 9:347-351 (2003)). Alternatively, the DNA encoding the ELOVL7 siRNA is in a vector.

Vectors are produced for example by cloning a ELOVL7 target sequence into an expression vector operatively-linked regulatory sequences flanking the ELOVL7 sequence in a manner that allows for expression (by transcription of the DNA molecule) of both strands (Lee, N. S., (2002) Nature Biotechnology 20: 500-505.). An RNA molecule that is antisense to ELOVL7 mRNA is transcribed by a first promoter (e.g., a promoter sequence 3' of the cloned DNA) and an RNA molecule that is the sense strand for the ELOVL7 mRNA is transcribed by a second promoter (e.g., a promoter sequence 5' of the cloned DNA). The sense and antisense strands hybridize in vivo to generate siRNA constructs for silencing of the ELOVL7 gene. Alternatively, two constructs are utilized to create the sense and antisense strands of a siRNA construct. Cloned ELOVL7 can encode a construct having secondary structure, e.g., hairpins, wherein a single transcript has both the sense and complementary antisense sequences from the target gene.

Furthermore, a loop sequence consisting of an arbitrary nucleotide sequence can be located between the sense and antisense sequence in order to form the hairpin loop structure. Thus, the present invention also provides siRNA having the general formula 5'-[A]-[B]-[A']-3', wherein [A] is a ribonucleotide sequence corresponding to a sequence that specifically hybridizes to an mRNA or a cDNA from a ELOVL7 gene. In preferred embodiments, [A] is a ribonucleotide sequence corresponding a sequence of nucleotides 3531-3549 (SEQ ID NO: 7) of SEQ ID NO: 14,

[B] is a ribonucleotide sequence consisting of about 3 to about 23 nucleotides, and

[A'] is a ribonucleotide sequence consisting of the complementary sequence of [A]. The loop sequence may consist of arbitrary sequence having preferably 3 to 23 nucleotide in length. The loop sequence, for example, can be selected from group consisting of following sequences (http://www.ambion.com/techlib/tb/tb_506.html). In the siRNA of the present invention, nucleotide "u" can be added to the 3' end of [A'], in order to enhance the inhibiting activity of the siRNA. The number of "u"s to be added is at least about 2, generally about 2 to about 10, preferably about 2 to about 5. Furthermore, loop sequence consisting of 23 nucleotides also provides active siRNA (Jacque, J.-M., et al., (2002) Nature 418: 435-438.).

CCC, CCACC or CCACACC: Jacque, J. M., et al., Nature, Vol. 418: 435-438 (2002);

UUCG: Lee, N. S., et al., (2002) Nature Biotechnology 20: 500-505.; Fruscoloni, P., et. al., Proc. Natl. Acad. Sci. USA 100(4): 1639-1644 (2003); and UUCAAGAGA: Dykxhoorn, D. M., et al., Nature Reviews Molecular Cell Biology 4: 457-467 (2002).

For example, preferable siRNAs having hairpin structure of the present invention are shown below. In the following structure, the loop sequence can be selected from group consisting of CCC, UUCG, CCACC, CCACACC, and UUCAAGAGA. Preferable loop sequence is UUCAAGAGA ("ttcaagaga" in DNA).

```
                    (for target sequence of SEQ ID NO: 7)
    caagcaacaacaacaacaa-[B]-uuguuguuguuguugcuug
```

The regulatory sequences flanking the ELOVL7 sequence are identical or are different, such that their expression can be modulated independently, or in a temporal or spatial manner. siRNAs are transcribed intracellularly by cloning the ELOVL7 gene templates into a vector containing, e.g., a RNA polymerase III transcription unit from the small nuclear RNA (snRNA) U6 or the human H1 RNA promoter. For introducing the vector into the cell, transfection-enhancing agent can be used. FuGENE (Rochediagnostices), Lipofectamine 2000 (Invitrogen), Oligofectamine (Invitrogen), and Nucleofector (Wako pure Chemical) are useful as the transfection-enhancing agent.

The nucleotide sequence of siRNAs may be designed using an siRNA design computer program available from the Ambion website (http://www.ambion.com/techlib/misc/siRNA_finder.html). Nucleotide sequences for the siRNA are selected by the computer program based on the following protocol:

Selection of siRNA Target Sites:
1. Beginning with the AUG start codon of the object transcript, scan downstream for AA dinucleotide sequences. Record the occurrence of each AA and the 3' adjacent 19 nucleotides as potential siRNA target sites. Tuschl, et al. Genes Dev 13(24): 3191-7 (1999), don't recommend against designing siRNA to the 5' and 3' untranslated regions (UTRs) and regions near the start codon (within 75 bases) as these may be richer in regulatory protein binding sites. UTR-binding proteins and/or translation initiation complexes may interfere with the binding of the siRNA endonuclease complex.
2. Compare the potential target sites to the human genome database and eliminate from consideration any target sequences with significant homology to other coding sequences. The homology search can be performed using BLAST, which can be found on the NCBI server at: www.ncbi.nlm.nih.gov/BLAST/ (Altschul S F, et al, Nucleic Acids Res. 1997; 25(17):3389-402; Altschul S F, et al, J Mol. Biol. 1990; 215(3):403-10).
3. Select qualifying target sequences for synthesis. At Ambion, preferably several target sequences can be selected along the length of the gene for evaluation.

Oligonucleotides and oligonucleotides complementary to various portions of ELOVL7 mRNA were tested in vitro for their ability to decrease production of ELOVL7 in tumor cells (e.g., using the PC3, LNCaP, 22Rv1 or DU145 PRC cell line) according to standard methods. A reduction in ELOVL7 gene product in cells contacted with the candidate siRNA composition compared to cells cultured in the absence of the candidate composition is detected using ELOVL7-specific antibodies or other detection strategies. Sequences which decrease production of ELOVL7 in in vitro cell-based or cell-free assays are then tested for there inhibitory effects on cell growth. Sequences which inhibit cell growth in in vitro cell-based assay are test in in vivo in rats or mice to confirm decreased ELOVL7 production and decreased tumor cell growth in animals with malignant neoplasms.

Also included in the invention are double-stranded molecules that include the nucleic acid sequence of target sequences, for example, nucleotides 3531-3549 (SEQ ID NO: 7) of SEQ ID NO: 14. In the present invention, the double-stranded molecule comprising a sense strand and an antisense strand, wherein the sense strand comprises a ribonucleotide sequence corresponding to SEQ ID NO: 7, and wherein the antisense strand comprises a ribonucleotide sequence which is complementary to said sense strand, wherein said sense strand and said antisense strand hybridize to each other to form said double-stranded molecule, and wherein said double-stranded molecule, when introduced into a cell expressing the ELOVL7 gene, inhibits expression of said gene. In the present invention, when the isolated nucleic acid is RNA or derivatives thereof, base "t" should be replaced with "u" in the nucleotide sequences. As used herein, the term "complementary" refers to Watson-Crick or Hoogsteen base pairing between nucleotides units of a nucleic acid molecule, and the term "binding" means the physical or chemical interaction between two nucleic acids or compounds or associated nucleic acids or compounds or combinations thereof.

Complementary nucleic acid sequences hybridize under appropriate conditions to form stable duplexes containing few or no mismatches. Furthermore, the sense strand and antisense strand of the isolated nucleotide of the present invention, can form double stranded nucleotide or hairpin loop structure by the hybridization. In a preferred embodiment, such duplexes contain no more than 1 mismatch for every 10 matches. In an especially preferred embodiment, where the strands of the duplex are fully complementary, such duplexes contain no mismatches. The nucleic acid molecule is less than 3815 nucleotides (for SEQ ID NO: 14) in length. For example, the nucleic acid molecule is less than 500, 200, or 75 nucleotides in length. Also included in the invention is a vector containing one or more of the nucleic acids described herein, and a cell containing the vectors. The isolated nucleic acids of the present invention are useful for siRNA against ELOVL7 or DNA encoding the siRNA. When the nucleic acids are used for siRNA or coding DNA thereof, the sense strand is preferably longer than about 19 nucleotides, and more preferably longer than about 21 nucleotides.

The antisense oligonucleotide or siRNA of the invention inhibit the expression of the polypeptide of the invention and is thereby useful for suppressing the biological activity of the polypeptide of the invention. Also, expression-inhibitors, comprising the antisense oligonucleotide or siRNA of the invention, are useful in the point that they can inhibit the biological activity of the polypeptide of the invention. Therefore, a composition comprising antisense oligonucleotide or siRNA of the present invention are useful in treating a PRC. Examples of ELOVL7 siRNA oligonucleotide which inhibit the expression in mammalian cells include the target sequence containing SEQ ID NO: 7. Furthermore, in order to enhance the inhibition activity of the siRNA, nucleotide "u" can be added to 3' end of the antisense strand of the target sequence. The number of "u"s to be added is at least about 2, generally about 2 to about 10, preferably about 2 to about 5. The added "u"s form single strand at the 3' end of the antisense strand of the siRNA.

Also, expression-inhibitors, comprising the antisense oligonucleotide or siRNA of the invention, are useful in the point that they can inhibit the biological activity of the polypeptide of the invention. Therefore, a composition comprising the antisense oligonucleotide or siRNA of the present invention is useful in treating a cell proliferative disease such as PRC.

Furthermore, the present invention provides ribozymes that inhibit the expression of the ELOVL7 polypeptide of the present invention.

Generally, ribozymes are classified into large ribozymes and small ribozymes. A large ribozyme is known as an enzyme that cleaves the phosphate ester bond of nucleic acids. After the reaction with the large ribozyme, the reacted site consists of a 5'-phosphate and 3'-hydroxyl group. The large ribozyme is further classified into (1) group I intron RNA catalyzing transesterification at the 5'-splice site by guanosine; (2) group II intron RNA catalyzing self-splicing through a two step reaction via lariat structure; and (3) RNA component of the ribonuclease P that cleaves the tRNA precursor at the 5' site through hydrolysis. On the other hand, small ribozymes have a smaller size (about 40 bp) compared to the large ribozymes and cleave RNAs to generate a 5'-hydroxyl group and a 2'-3' cyclic phosphate. Hammerhead type ribozymes (Koizumi et al., FEBS Lett 228: 225 (1988)) and hairpin type ribozymes (Buzayan, Nature 323: 349-53 (1986); Kikuchi and Sasaki, Nucleic Acids Res 19: 6751 (1992)) are included in the small ribozymes. Methods for designing and constructing ribozymes are known in the art (see Koizumi et al., FEBS Lett 228: 225 (1988); Koizumi et al., Nucleic Acids Res 17: 7059 (1989); Kikuchi and Sasaki, Nucleic Acids Res 19: 6751 (1992)). Thus, ribozymes inhibiting the expression of the polypeptides of the present invention can also be constructed based on their sequence information (SEQ ID NO: 14) and these conventional methods.

Ribozymes against ELOVL7 gene inhibit the expression of over-expressed ELOVL7 protein and is thus useful for suppressing the biological activity of the protein. Therefore, the ribozymes are useful in treating or preventing PRC.

Diagnosing Prostate Cancer

Moreover, the present invention provides a method for diagnosing cell proliferative disease such as PRC using the expression level of the genes or the activity levels of the polypeptides of the present invention as diagnostic markers.

This in some embodiments, the diagnosing method comprises the steps of: (a) detecting the expression level of the ELOVL7 gene of the present invention; and (b) relating an elevation of the expression level to PRC.

The expression levels of the ELOVL7 gene in a biological sample can be estimated by quantifying mRNA corresponding to or protein encoded by the ELOVL7 gene. Quantification methods for mRNA are known to those skilled in the art. For example, the levels of mRNAs corresponding to the ELOVL7 gene can be estimated by Northern blotting or RT-PCR. Since the full-length nucleotide sequences of the ELOVL7 genes are shown in SEQ ID NO: 14, anyone skilled in the art can design the nucleotide sequences for probes or primers to quantify the ELOVL7 gene.

Also the expression level of the ELOVL7 gene can be analyzed based on the quantity of protein encoded by the gene. A method for determining the quantity of the ELOVL7 protein is shown in below. For example, immunoassay methods are useful for the determination of the proteins in biological materials. Any biological materials can be used as the biological sample for the determination of the protein or it's activity so long as the marker gene (ELOVL7 gene) is expressed in the sample of a PRC patient. For example, prostate duct epithelium can be mentioned as such biological sample. However, bodily fluids such as blood and urine may be also analyzed.

Expression levels of the ELOVL7 gene or protein levels of the ELOVL7 polypeptide in a biological sample are estimated and compared with those in a normal sample (e.g., a sample derived from a non-diseased subject). When such a comparison shows that the expression level of the target gene or protein level is higher than those in the normal sample, the subject is judged to be affected with PRC. The expression level of ELOVL7 gene in the biological samples from a normal subject and subject to be diagnosed may be determined at the same time. Alternatively, normal ranges of the expression or protein levels can be determined by a statistical method based on the results obtained by analyzing the expression level of the gene in samples previously collected from a control group. A result obtained by comparing the sample of a subject is compared with the normal range; when the result does not fall within the normal range, the subject is judged to be affected with or is at risk of developing PRC.

In the present invention, a diagnostic agent for diagnosing cell proliferative disease, such as PRC, is also provided. The diagnostic agent of the present invention comprises a compound that binds to a polynucleotide or a polypeptide of the present invention. Preferably, an oligonucleotide that hybridizes to the polynucleotide of the present invention or an antibody that binds to the polypeptide of the present invention may be used as such a compound.

The present method of diagnosing PRC may be applied for assessing the efficacy of treatment of PRC in a subject. According to the method, a biological sample, such as a test cell population, is obtained from a subject undergoing treatment for PRC. The method for assessment can be conducted according to conventional methods of diagnosing PRC.

If desired, biological samples are obtained from the subject at various time points before, during or after the treatment. The expression level of ELOVL7 gene, in the biological sample is then determined and compared to a control level derived, for example, from a reference cell population which includes cells whose state of PRC (i.e., cancerous cell or non-cancerous cell) is known. The control level is determined in a biological sample that has not been exposed to the treatment.

If the control level is derived from a biological sample which contains no cancerous cell, a similarity between the expression level in the subject-derived biological sample and the control level indicates that the treatment is efficacious. A difference between the expression level of the ELOVL7 gene in the subject-derived biological sample and the control level indicates a less favorable clinical outcome or prognosis.

The term "efficacious" refers that the treatment leads to a reduction in the expression of a pathologically up-regulated gene (ELOVL7 gene) or a decrease in size, prevalence or proliferating potential of PRC cells in a subject. When a treatment is applied prophylactically, "efficacious" indicates that the treatment retards or prevents occurrence of PRC. The assessment of PRC can be made using standard clinical protocols. Furthermore, the efficaciousness of a treatment is determined in association with any known method for diagnosing or treating PRC.

Moreover, the present method of diagnosing PRC may also be applied for assessing the prognosis of a subject with PRC by comparing the expression level of ELOVL7 gene in a patient-derived biological sample, such as test cell population, to a control level. Alternatively, the expression level of ELOVL7 gene in a biological sample derived from patients may be measured over a spectrum of disease stages to assess the prognosis of the patient.

An increase in the expression level of ELOVL7 gene compared to a normal control level indicates less favorable prognosis. A decrease in the expression level of ELOVL7 gene indicates a more favorable prognosis for the patient.

Screening Compounds

Using the ELOVL7 gene, proteins encoded by the gene or transcriptional regulatory region of the gene, compounds can be screened that alter the expression of the gene or the biological activity of a polypeptide encoded by the gene. Such compounds are used as pharmaceuticals for treating or preventing PRC.

Therefore, the present invention provides a method of screening for a compound for treating or preventing PRC using the polypeptide of the present invention. An embodiment of this screening method comprises the steps of: (a) contacting a test compound with a polypeptide of the present invention; (b) detecting the binding activity between the polypeptide of the present invention and the test compound; and (c) selecting the compound that binds to the polypeptide of the present invention.

The polypeptide of the present invention to be used for screening may be a recombinant polypeptide or a protein derived from the nature or a partial peptide thereof. The polypeptide of the present invention to be contacted with a test compound can be, for example, a purified polypeptide, a soluble protein, a form bound to a carrier or a fusion protein fused with other polypeptides.

As a method of screening for proteins, for example, that bind to the polypeptide of the present invention using the polypeptide of the present invention, many methods well known by a person skilled in the art can be used. Such a screening can be conducted by, for example, immunoprecipitation method, specifically, in the following manner. The gene encoding the polypeptide of the present invention is expressed in host (e.g., animal) cells and so on by inserting the gene to an expression vector for foreign genes, such as pSV2neo, pcDNA I, pcDNA3.1, pCAGGS and pCD8. The promoter to be used for the expression may be any promoter that can be used commonly and include, for example, the SV40 early promoter (Rigby in Williamson (ed.), Genetic Engineering, vol. 3. Academic Press, London, 83-141 (1982)), the EF-α promoter (Kim et al., Gene 91: 217-23 (1990)), the CAG promoter (Niwa et al., Gene 108: 193-200 (1991)), the RSV LTR promoter (Cullen, Methods in Enzymology 152: 684-704 (1987)) the SRα promoter (Takebe et al., Mol Cell Biol 8: 466 (1988)), the CMV immediate early promoter (Seed and Aruffo, Proc Natl Acad Sci USA 84: 3365-9 (1987)), the SV40 late promoter (Gheysen and Fiers, J Mol Appl Genet. 1: 385-94 (1982)), the Adenovirus late promoter (Kaufman et al., Mol Cell Biol 9: 946-58 (1989)), the HSV TK promoter and so on. The introduction of the gene into host cells to express a foreign gene can be performed according to any methods, for example, the electroporation method (Chu et al., Nucleic Acids Res 15: 1311-26 (1987)), the calcium phosphate method (Chen and Okayama, Mol Cell Biol 7: 2745-52 (1987)), the DEAE dextran method (Lopata et al., Nucleic Acids Res 12: 5707-17 (1984); Sussman and Milman, Mol Cell Biol 4: 1641-3 (1984)), the Lipofectin method (Derijard B., et al., Cell 7: 1025-37 (1994); Lamb et al., Nature Genetics 5: 22-30 (1993): Rabindran et al., Science 259: 230-4 (1993)) and so on. The polypeptide of the present invention can be expressed as a fusion protein comprising a recognition site (epitope) of a monoclonal antibody by introducing the epitope of the monoclonal antibody, whose specificity has been revealed, to the N- or C-terminus of the polypeptide of the present invention. A commercially available epitope-antibody system can be used (Experimental Medicine 13: 85-90 (1995)). Vectors which can express a fusion protein with, for example, β-galactosidase, maltose binding protein, glutathione S-transferase, green florescence protein (GFP) and so on by the use of its multiple cloning sites are commercially available.

A fusion protein prepared by introducing only small epitopes consisting of several to a dozen amino acids so as not to change the property of the polypeptide of the present invention by the fusion is also reported. Epitopes, such as polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), E-tag (an epitope on monoclonal phage) and such, and monoclonal antibodies recognizing them can be used as the epitope-antibody system for screening proteins binding to the polypeptide of the present invention (Experimental Medicine 13: 85-90 (1995)).

In immunoprecipitation, an immune complex is formed by adding these antibodies to cell lysate prepared using an appropriate detergent. The immune complex consists of the polypeptide of the present invention, a polypeptide comprising the binding ability with the polypeptide, and an antibody. Immunoprecipitation can be also conducted using antibodies against the polypeptide of the present invention, besides using antibodies against the above epitopes, which antibodies can be prepared as described above.

An immune complex can be precipitated, for example by Protein A sepharose or Protein G sepharose when the antibody is a mouse IgG antibody. If the polypeptide of the present invention is prepared as a fusion protein with an epitope, such as GST, an immune complex can be formed in the same manner as in the use of the antibody against the polypeptide of the present invention, using a substance specifically binding to these epitopes, such as glutathione-Sepharose 4B.

Immunoprecipitation can be performed by following or according to, for example, the methods in the literature (Harlow and Lane, Antibodies, 511-52, Cold Spring Harbor Laboratory publications, New York (1988)).

SDS-PAGE is commonly used for analysis of immunoprecipitated proteins and the bound protein can be analyzed by the molecular weight of the protein using gels with an appropriate concentration. Since the protein bound to the polypeptide of the present invention is difficult to detect by a common staining method, such as Coomassie staining or silver staining, the detection sensitivity for the protein can be improved by culturing cells in culture medium containing radioactive isotope, $^{35}$S-methionine or $^{35}$S-cystein, labeling proteins in the cells, and detecting the proteins. The target protein can be purified directly from the SDS-polyacrylamide gel and its sequence can be determined, when the molecular weight of a protein has been revealed.

As a method for screening proteins binding to the polypeptide of the present invention using the polypeptide, for example, West-Western blotting analysis (Skolnik et al., Cell 65: 83-90 (1991)) can be used. Specifically, a protein binding to the polypeptide of the present invention can be obtained by preparing a cDNA library from cells, tissues, organs (for example, tissues such as prostate), or cultured cells (e.g., PC3, DU145, LNCaP, 22Rv11) expected to express a protein binding to the polypeptide of the present invention using a phage vector (e.g., ZAP), expressing the protein on LB-agarose, fixing the protein expressed on a filter, reacting the purified and labeled polypeptide of the present invention with the above filter, and detecting the plaques expressing proteins bound to the polypeptide of the present invention according to the label. The polypeptide of the invention may be labeled by utilizing the binding between biotin and avidin, or by utilizing an antibody that specifically binds to the polypeptide of the present invention, or a peptide or polypeptide (for example, GST) that is fused to the polypeptide of the present invention. Methods using radioisotope or fluorescence and such may be also used.

Alternatively, in another embodiment of the screening method of the present invention, a two-hybrid system utilizing cells may be used ("MATCHMAKER Two-Hybrid system", "MATCHMAKER Mammalian Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Stemglanz, Trends Genet. 10: 286-92 (1994)").

In the two-hybrid system, the polypeptide of the invention is fused to the SRF-binding region or GAL4-binding region and expressed in yeast cells. A cDNA library is prepared from cells expected to express a protein binding to the polypeptide of the invention, such that the library, when expressed, is fused to the VP16 or GAL4 transcriptional activation region. The cDNA library is then introduced into the above yeast cells and the cDNA derived from the library is isolated from the positive clones detected (when a protein binding to the polypeptide of the invention is expressed in yeast cells, the binding of the two activates a reporter gene, making positive clones detectable). A protein encoded by the cDNA can be prepared by introducing the cDNA isolated above to E. coli and expressing the protein.

As a reporter gene, for example, Ade2 gene, lacZ gene, CAT gene, luciferase gene and such can be used in addition to the HIS3 gene.

A compound binding to the polypeptide of the present invention can also be screened using affinity chromatography. For example, the polypeptide of the invention may be immobilized on a carrier of an affinity column, and a test compound, containing a protein capable of binding to the polypeptide of the invention, is applied to the column. A test compound herein may be, for example, cell extracts, cell lysates, etc. After loading the test compound, the column is washed, and compounds bound to the polypeptide of the invention can be prepared.

When the test compound is a protein, the amino acid sequence of the obtained protein is analyzed, an oligo DNA is synthesized based on the sequence, and cDNA libraries are screened using the oligo DNA as a probe to obtain a DNA encoding the protein.

A biosensor using the surface plasmon resonance phenomenon may be used as a mean for detecting or quantifying the bound compound in the present invention. When such a biosensor is used, the interaction between the polypeptide of the invention and a test compound can be observed real-time as a surface plasmon resonance signal, using only a minute amount of polypeptide and without labeling (for example, BIAcore, Pharmacia). Therefore, it is possible to evaluate the binding between the polypeptide of the invention and a test compound using a biosensor such as BIAcore.

The methods of screening for molecules that bind when the immobilized polypeptide of the present invention is exposed to synthetic chemical compounds, or natural substance banks or a random phage peptide display library, and the methods of screening using high-throughput based on combinatorial chemistry techniques (Wrighton et al., Science 273: 458-64 (1996); Verdine, Nature 384: 11-13 (1996); Hogan, Nature 384: 17-9 (1996)) to isolate not only proteins but chemical compounds that bind to the protein of the present invention (including agonist and antagonist) are well known to one skilled in the art.

Alternatively, the present invention provides a method of screening for a compound for treating or preventing PRC using the polypeptide of the present invention comprising the steps as follows:

(a) contacting a test compound with the polypeptide of the present invention;

(b) detecting the biological activity of the polypeptide of step (a); and (c) selecting a compound that suppresses the biological activity of the polypeptide in comparison with the biological activity detected in the absence of the test compound.

Since the ELOVL7 protein of the present invention have the activity of promoting cell proliferation of PRC cells, a compound which inhibits this activity of this protein of the present invention can be screened using this activity as an index.

Any polypeptides can be used for screening so long as they comprise the biological activity of the ELOVL7 protein. Such biological activity include cell-proliferating activity of the human ELOVL7 protein. For example, a human ELOVL7 protein can be used and polypeptides functionally equivalent to these proteins can also be used. Such polypeptides may be expressed endogenously or exogenously by cells.

Alternatively, the assay can be carried by directly detecting the fatty acid elongation activity of ELOVL7 proteins in the presence of the test compound. In these embodiments, in vitro activity of the ELOVL7 is detected using methods known in the art. For example, microsomes can be isolated from the cells expressing an ELOVL7 polypeptide of the invention by differential centrifugation generally using the procedures described by Moon et al (Moon Y A, et al. J Biol Chem. 2001; 276:45358-45366.). Preferred methods for preparing the microsomes are described below. Typically, the reaction mixtures will contain microsomes containing an ELOVL7 polypeptide of the invention (e.g., SEQ ID NO: 15, or polypeptide that is at least about 80% identical to SEQ ID NO: 15) and appropriate reagents for carrying out the assay. Such reagents may include, for example, a fatty acid substrate (e.g., Arachidoyl-CoA), Malonyl-CoA, NADPH, and a reagent for detecting the elongation product. Each fatty acid level in the samples can be analyzed using e.g., gas chromatography mass spectrometry as described below. Kits comprising the above reagents useful for carrying out the fatty acid elongation activity assays of the invention can also be prepared.

The compound isolated by this screening is a candidate for antagonists of the polypeptide of the present invention. The term "agonist" refers to molecules that activate the function of the polypeptide of the present invention by binding thereto. Likewise, the term "antagonist" refers to molecules that inhibit the function of the polypeptide of the present invention by binding thereto. Moreover, a compound isolated by this screening as "agonist" is a candidate for compounds which inhibit the in vivo interaction of the polypeptide of the present invention with molecules (including DNAs and proteins).

When the biological activity to be detected in the present method is cell proliferation, it can be detected, for example, by preparing cells which express the polypeptide of the present invention, culturing the cells in the presence of a test compound, and determining the speed of cell proliferation, measuring the cell cycle and such, as well as by measuring the colony forming activity as described in the Examples.

In a further embodiment, the present invention provides methods for screening compounds for treating or preventing PRC. As discussed in detail above, by controlling the expression levels of the ELOVL7, one can control the onset and progression of PRC. Thus, compounds that may be used in the treatment or prevention of PRC can be identified through screenings that use the expression levels of ELOVL7 as indices. In the context of the present invention, such screening may comprise, for example, the following steps:
  a) contacting a test compound with a cell expressing the ELOVL7; and
  b) selecting a compound that reduces the expression level of ELOVL7 in comparison with the expression level detected in the absence of the test compound.

Cells expressing at least one of the ELOVL7 include, for example, cell lines established from PRCs; such cells can be used for the above screening of the present invention (e.g., PC3, DU145, LNCaP, 22Rv1). The expression level can be estimated by methods well known to one skilled in the art. In the method of screening, a compound that reduces the expression level of ELOVL7 can be selected as candidate agents to be used for the treatment or prevention of PRC.

Alternatively, the screening method of the present invention may comprise the following steps:
  a) contacting a test compound with a cell into which a vector comprising the transcriptional regulatory region of marker gene and a reporter gene that is expressed under the control of the transcriptional regulatory region has been introduced, wherein the marker gene is ELOVL7,
  b) measuring the expression level or activity of said reporter gene; and
  c) selecting a compound that reduces the expression level or activity of said reporter gene as compared to a control.

Suitable reporter genes and host cells are well known in the art. The reporter construct required for the screening can be prepared by using the transcriptional regulatory region of a marker gene. When the transcriptional regulatory region of a marker gene has been known to those skilled in the art, a reporter construct can be prepared by using the previous sequence information. When the transcriptional regulatory region of a marker gene remains unidentified, a nucleotide segment containing the transcriptional regulatory region can be isolated from a genome library based on the nucleotide sequence information of the marker gene.

Examples of supports that may be used for binding proteins include insoluble polysaccharides, such as agarose, cellulose and dextran; and synthetic resins, such as polyacrylamide, polystyrene and silicon; preferably commercial available beads and plates (e.g., multi-well plates, biosensor chip, etc.) prepared from the above materials may be used. When using beads, they bay be filled into a column.

The binding of a protein to a support may be conducted according to routine methods, such as chemical bonding and physical adsorption. Alternatively, a protein may be bound to a support via antibodies specifically recognizing the protein. Moreover, binding of a protein to a support can be also conducted by means of avidin and biotin.

The binding between proteins is carried out in buffer, for example, but are not limited to, phosphate buffer and Tris buffer, as long as the buffer does not inhibit the binding between the proteins.

In the present invention, a biosensor using the surface plasmon resonance phenomenon may be used as a mean for detecting or quantifying the bound protein. When such a biosensor is used, the interaction between the proteins can be observed real-time as a surface plasmon resonance signal, using only a minute amount of polypeptide and without labeling (for example, BIAcore, Pharmacia).

Alternatively, ELOVL7 polypeptide may be labeled, and the label of the bound protein may be used to detect or measure the bound protein. Specifically, after pre-labeling one of the proteins, the labeled protein is contacted with the other protein in the presence of a test compound, and then bound proteins are detected or measured according to the label after washing.

Labeling substances such as radioisotope (e.g., $^{3}H$, $^{14}C$, $^{32}P$, $^{33}P$, $^{35}S$, $^{125}I$, $^{131}I$), enzymes (e.g., alkaline phosphatase, horseradish peroxidase, β-galactosidase, β-glucosidase), fluorescent substances (e.g., fluorescein isothiosyanete (FITC), rhodamine) and biotin/avidin, may be used for the labeling of a protein in the present method. When the protein is labeled with radioisotope, the detection or measurement can be carried out by liquid scintillation. Alternatively, proteins labeled with enzymes can be detected or measured by adding a substrate of the enzyme to detect the enzymatic change of the substrate, such as generation of color, with absorptiometer. Further, in case where a fluorescent substance is used as the label, the bound protein may be detected or measured using fluorophotometer.

In case of using an antibody in the present screening, the antibody is preferably labeled with one of the labeling substances mentioned above, and detected or measured based on the labeling substance. Alternatively, the antibody against the ELOVL7 polypeptide or actin may be used as a primary antibody to be detected with a secondary antibody that is labeled with a labeling substance. Furthermore, the antibody bound to the protein in the screening of the present invention may be detected or measured using protein G or protein A column.

Any test compound, for example, cell extracts, cell culture supernatant, products of fermenting microorganism, extracts from marine organism, plant extracts, purified or crude proteins, peptides, non-peptide compounds, synthetic micromolecular compounds and natural compounds can be used in the screening methods of the present invention. The test compound of the present invention can be also obtained using any of the numerous approaches in combinatorial library methods known in the art, including (1) biological libraries, (2) spatially addressable parallel solid phase or solution phase libraries, (3) synthetic library methods requiring deconvolution, (4) the "one-bead one-compound" library method and (5) synthetic library methods using affinity chromatography selection. The biological library methods using affinity chromatography selection is limited to peptide libraries, while the other four approaches are applicable to peptide, non-peptide oligomer or small molecule libraries of compounds (Lam (1997) Anticancer Drug Des. 12: 145). Examples of methods for the synthesis of molecular libraries can be found in the art (DeWitt et al. (1993) Proc. Natl. Acad. Sci. USA 90: 6909; Erb et al. (1994) Proc. Natl. Acad. Sci. USA 91: 11422; Zuckermann et al. (1994) J. Med. Chem. 37: 2678; Cho et al. (1993) Science 261: 1303; Carell et al. (1994) Angew. Chem. Int. Ed. Engl. 33: 2059; Carell et al. (1994) Angew. Chem. Int. Ed. Engl. 33: 2061; Gallop et al. (1994) J. Med. Chem. 37: 1233). Libraries of compounds may be presented in solution (see Houghten (1992) Biotechniques 13: 412) or on beads (Lam (1991) Nature 354: 82), chips (Fodor (1993) Nature 364: 555), bacteria (U.S. Pat. No. 5,223,409), spores (U.S. Pat. Nos. 5,571,698; 5,403,484, and 5,223,409), plasmids (Cull et al. (1992) Proc. Natl. Acad. Sci. USA 89: 1865) or phage (Scott and Smith (1990) Science 249: 386; Devlin (1990) Science 249: 404; Cwirla et al. (1990) Proc. Natl. Acad. Sci. USA 87: 6378; Felici (1991) J. Mol. Biol. 222: 301; US Pat. Application 20020103360).

A compound isolated by the screening methods of the present invention is a candidate for drugs which inhibit the activity of the polypeptide of the present invention, for treating or preventing diseases attributed to, for example, cell proliferative diseases, such as PRC. A compound in which a part of the structure of the compound obtained by the present screening methods of the present invention is converted by addition, deletion and/or replacement, is included in the compounds obtained by the screening methods of the present invention.

Pharmaceutical Compositions for Treating or Preventing Prostate Cancer

The present invention provides compositions for treating or preventing prostate cancer comprising any of the compounds selected by the screening methods of the present invention.

When administrating a compound isolated by the screening methods of the present invention as a pharmaceutical for humans or other mammals, such as mice, rats, guinea-pigs, rabbits, cats, dogs, sheep, pigs, cattle, monkeys, baboons, chimpanzees, for treating a cell proliferative disease (e.g., PRC) the isolated compound can be directly administered or can be formulated into a dosage form using known pharmaceutical preparation methods. For example, according to the need, the drugs can be taken orally, as sugarcoated tablets, capsules, elixirs and microcapsules; or non-orally, in the form of injections of sterile solutions or suspensions with water or any other pharmaceutically acceptable liquid. For example, the compounds can be mixed with pharmacologically acceptable carriers or medium, specifically, sterilized water, physiological saline, plant-oil, emulsifiers, suspending agents, surfactants, stabilizers, flavoring agents, excipients, vehicles, preservatives, binders and such, in a unit dose form required for generally accepted drug implementation. The amount of active ingredients in these preparations makes a suitable dosage within the indicated range acquirable.

Examples of additives that can be mixed to tablets and capsules are, binders such as gelatin, corn starch, tragacanth gum and arabic gum; excipients such as crystalline cellulose; swelling agents such as corn starch, gelatin and alginic acid; lubricants such as magnesium stearate; sweeteners such as sucrose, lactose or saccharin; flavoring agents such as peppermint, Gaultheria adenothrix oil and cherry. When the unit dosage form is a capsule, a liquid carrier, such as oil, can also be further included in the above ingredients. Sterile composites for injections can be formulated following normal drug implementations using vehicles such as distilled water used for injections.

Physiological saline, glucose, and other isotonic liquids including adjuvants, such as D-sorbitol, D-mannose, D-mannitol and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80 (TM) and HCO-50.

Sesame oil or Soy-bean oil can be used as a oleaginous liquid and may be used in conjunction with benzyl benzoate or benzyl alcohol as a solubilizers and may be formulated with a buffer, such as phosphate buffer and sodium acetate buffer; a pain-killer, such as procaine hydrochloride; a stabilizer, such as benzyl alcohol, phenol; and an anti-oxidant. The prepared injection may be filled into a suitable ampule.

Methods well known to one skilled in the art may be used to administer the inventive pharmaceutical compound to patients, for example as intraarterial, intravenous, percutaneous injections and also as intranasal, transbronchial, intramuscular or oral administrations. The dosage and method of administration vary according to the body-weight and age of a patient and the administration method; however, one skilled in the art can routinely select them. If said compound is encodable by a DNA, the DNA can be inserted into a vector for gene therapy and the vector administered to perform the therapy. The dosage and method of administration vary according to the body-weight, age, and symptoms of a patient but one skilled in the art can select them suitably.

For example, although there are some differences according to the symptoms, the dose of a compound that binds with the polypeptide of the present invention and regulates its activity is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kgs of body-weight.

Furthermore, the present invention provides pharmaceutical compositions for treating or preventing PRC comprising active ingredients that inhibits the expression of ELOVL7 gene. Such active ingredients include antisense polynucleotides, siRNAs or ribozymes against the ELOVL7 gene or derivatives, such as expression vector, of the antisense polynucleotides, siRNAs or ribozymes.

These active ingredients can be made into an external preparation, such as a liniment or a poultice, by mixing with a suitable base material which is inactive against the derivatives. Also, as needed, they can be formulated into tablets, powders, granules, capsules, liposome capsules, injections, solutions, nose-drops and freeze-drying agents by adding excipients, isotonic agents, solubilizers, stabilizers, preservatives, pain-killers and such. These can be prepared according to conventional methods.

The active ingredient is given to the patient by directly applying onto the ailing site or by injecting into a blood vessel so that it will reach the site of ailment. A mounting medium can also be used to increase durability and membrane-permeability. Examples of mounting medium includes liposome, poly-L-lysine, lipid, cholesterol, lipofectin or derivatives of these.

The dosage of such compositions of the present invention can be adjusted suitably according to the patient's condition and used in desired amounts. For example, a dose range of 0.1 to 100 mg/kg, preferably 0.1 to 50 mg/kg can be administered.

Another embodiment of the present invention is a composition for treating or preventing PRC comprising an antibody against a polypeptide encoded by the ELOVL7 gene or fragments of the antibody that bind to the polypeptide.

Although there are some differences according to the symptoms, the dose of an antibody or fragments thereof for treating or preventing PRC is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the condition of the patient, symptoms of the disease and method of administration, it is convenient to intravenously inject a dose of about 0.01 mg to about 30 mg per day, preferably about 0.1 to about 20 mg per day and more preferably about 0.1 to about 10 mg per day. Also in the case of other animals too, it is possible to administer an amount converted to 60 kg of body-weight.

Methods for Treating or Preventing Prostate Cancer

The invention provides a method for treating or preventing PRC in a subject. Therapeutic compounds are administered prophylactically or therapeutically to subject suffering from or at risk of (or susceptible to) developing PRC. Such subjects are identified using standard clinical methods or by detecting an aberrant expression level or activity of ELOVL7. Prophylactic administration occurs prior to the manifestation of overt clinical symptoms of disease, such that a disease or disorder is prevented or, alternatively, delayed in its progression.

The therapeutic method includes decreasing the expression or function of ELOVL7 gene. In these methods, the subject is treated with an effective amount of a compound, which decreases the over-expressed genes (ELOVL7 gene) in the subject. Administration can be systemic or local. Therapeutic compounds include compounds that decrease the expression level of such gene endogenously existing in the PRCous cells (i.e., compounds that down-regulate the expression of the over-expressed gene). Administration of such therapeutic compounds counter the effects of aberrantly-over expressed gene in the subject's cells and are expected to improve the clinical condition of the subject. Such compounds can be obtained by the screening method of the present invention described above.

The expression of ELOVL7 gene may be also inhibited in any of several ways known in the art including administering to the subject a nucleic acid that inhibits or antagonizes the expression of the gene. Antisense oligonucleotides, siRNA or ribozymes which disrupts expression of the gene can be used for inhibiting the expression of the genes.

As noted above, antisense-oligonucleotides corresponding to the nucleotide sequence of ELOVL7 gene can be used to reduce the expression level of the ELOVL7 gene. Specifically, the antisense-oligonucleotides of the present invention may act by binding to the polypeptide encoded by the ELOVL7 gene, or mRNAs corresponding thereto, thereby inhibiting the transcription or translation of the gene, promoting the degradation of the mRNAs, and/or inhibiting the expression of protein encoded by the gene, and finally inhibiting the function of the ELOVL7 protein.

An antisense-oligonucleotides and derivatives thereof can be made into an external preparation, such as a liniment or a poultice, by mixing with a suitable base material which is inactive against the derivative and used in the method for treating or preventing PRC of the present invention.

The nucleic acids that inhibit one or more gene products of over-expressed genes also include small interfering RNAs (siRNA) comprising a combination of a sense strand nucleic acid and an antisense strand nucleic acid of the nucleotide sequence encoding the ELOVL7 gene. Standard techniques of introducing siRNA into the cell can be used in the treatment or prevention of the present invention, including those in which DNA is a template from which RNA is transcribed. The siRNA is constructed such that a single transcript has both the sense and complementary antisense sequences from the target gene, e.g., a hairpin.

The method is used to suppress gene expression of a cell with up-regulated expression of the ELOVL7 gene. Binding of the siRNA to the ELOVL7 gene transcript in the target cell results in a reduction of ELOVL7 protein production by the cell.

The nucleic acids that inhibit a gene product of over-expressed gene also include ribozymes against the over-expressed gene (ELOVL7 gene).

Moreover, the present invention provides a method for treating or preventing a cell proliferative disease, such as PRC, using an antibody against the polypeptide of the present invention. According to the method, a pharmaceutically effective amount of an antibody against the polypeptide of the present invention is administered. Since the expression of the ELOVL7 protein are up-regulated in PRC cells and the suppression of the expression of these proteins leads to the decrease in cell proliferating activity, it is expected that cell proliferative diseases can be treated or prevented by binding the antibody and these proteins. Thus, an antibody against the polypeptide of the present invention is administered at a dosage sufficient to reduce the activity of the protein of the present invention, which is in the range of 0.1 to about 250 mg/kg per day. The dose range for adult humans is generally from about 5 mg to about 17.5 g/day, preferably about 5 mg to about 10 g/day, and most preferably about 100 mg to about 3 g/day.

Alternatively, an antibody binding to a cell surface marker specific for tumor cells can be used as a tool for drug delivery. For example, the antibody conjugated with a cytotoxic agent is administered at a dosage sufficient to injure tumor cells.

The present invention also relates to a method of inducing anti-tumor immunity comprising the step of administering ELOVL7 protein or an immunologically active fragment thereof, or a polynucleotide encoding the protein or fragments thereof. The ELOVL7 protein or the immunologically active fragments thereof are useful as vaccines against cell proliferative diseases such as PRC. In some cases the proteins or fragments thereof may be administered in a form bound to the T cell receptor (TCR) or presented by an antigen presenting cell (APC), such as macrophage, dendritic cell (DC), or B-cells. Due to the strong antigen presenting ability of DC, the use of DC is most preferable among the APCs.

In the present invention, vaccine against cell proliferative disease refers to a substance that has the function to induce anti-tumor immunity upon inoculation into animals. In general, anti-tumor immunity includes immune responses such as follows:

induction of cytotoxic lymphocytes against tumors,
induction of antibodies that recognize tumors, and
induction of anti-tumor cytokine production.

Therefore, when a certain protein induces any one of these immune responses upon inoculation into an animal, the protein is decided to have anti-tumor immunity inducing effect. The induction of the anti-tumor immunity by a protein can be detected by observing in vivo or in vitro the response of the immune system in the host against the protein.

For example, a method for detecting the induction of cytotoxic T lymphocytes is well known. A foreign substance that enters the living body is presented to T cells and B cells by the action of antigen presenting cells (APCs). T cells that respond to the antigen presented by APC in antigen specific manner differentiate into cytotoxic T cells (or cytotoxic T lymphocytes; CTLs) due to stimulation by the antigen, and then proliferate (this is referred to as activation of T cells). Therefore, CTL induction by a certain peptide can be evaluated by presenting the peptide to T cell by APC, and detecting the induction of CTL. Furthermore, APC has the effect of activating CD4+ T cells, CD8+ T cells, macrophages, eosinophils, and NK cells. Since CD4+ T cells and CD8+ T cells are also important in anti-tumor immunity, the anti-tumor immunity inducing action of the peptide can be evaluated using the activation effect of these cells as indicators.

A method for evaluating the inducing action of CTL using dendritic cells (DCs) as APC is well known in the art. DC is a representative APC having the strongest CTL inducing action among APCs. In this method, the test polypeptide is initially contacted with DC, and then this DC is contacted with T cells. Detection of T cells having cytotoxic effects against the cells of interest after the contact with DC shows that the test polypeptide has an activity of inducing the cytotoxic T cells. Activity of CTL against tumors can be detected, for example, using the lysis of $^{51}$Cr-labeled tumor cells as the indicator. Alternatively, the method of evaluating the degree of tumor cell damage using $^3$H-thymidine uptake activity or LDH (lactose dehydrogenase)-release as the indicator is also well known.

Apart from DC, peripheral blood mononuclear cells (PBMCs) may also be used as the APC. The induction of CTL is reported that it can be enhanced by culturing PBMC in the presence of GM-CSF and IL-4. Similarly, CTL has been shown to be induced by culturing PBMC in the presence of keyhole limpet hemocyanin (KLH) and IL-7.

The test polypeptides confirmed to possess CTL inducing activity by these methods are polypeptides having DC activation effect and subsequent CTL inducing activity. Therefore, polypeptides that induce CTL against tumor cells are useful as vaccines against tumors. Furthermore, APC that acquired the ability to induce CTL against tumors by contacting with the polypeptides are useful as vaccines against tumors. Furthermore, CTL that acquired cytotoxicity due to presentation of the polypeptide antigens by APC can be also used as vaccines against tumors. Such therapeutic methods for tumors using anti-tumor immunity due to APC and CTL are referred to as cellular immunotherapy.

Generally, when using a polypeptide for cellular immunotherapy, efficiency of the CTL-induction is known to increase by combining a plurality of polypeptides having different structures and contacting them with DC. Therefore, when stimulating DC with protein fragments, it is advantageous to use a mixture of multiple types of fragments.

Alternatively, the induction of anti-tumor immunity by a polypeptide can be confirmed by observing the induction of antibody production against tumors. For example, when antibodies against a polypeptide are induced in a laboratory animal immunized with the polypeptide and when growth of tumor cells is suppressed by those antibodies, the polypeptide can be determined to have an ability to induce anti-tumor immunity.

Anti-tumor immunity is induced by administering the vaccine of this invention, and the induction of anti-tumor immunity enables treatment and prevention of cell proliferating diseases, such as PRC. Therapy against cancer or prevention of the onset of cancer includes any of the steps, such as inhibition of the growth of cancerous cells, involution of cancer and suppression of occurrence of cancer. Decrease in mortality of individuals having cancer, decrease of tumor markers in the blood, alleviation of detectable symptoms accompanying cancer and such are also included as the effect of therapy or prevention of cancer. Such therapeutic and preventive effects are preferably statistically significant. For example, in observation, at a significance level of 5% or less, wherein the therapeutic or preventive effect of a vaccine against cell proliferative diseases is compared to a control without vaccine administration. For example, Student's t-test, the Mann-Whitney U-test or ANOVA may be used for statistical analysis.

The above-mentioned protein having immunological activity or a vector encoding the protein may be combined with an adjuvant. An adjuvant refers to a compound that enhances the immune response against the protein when administered together (or successively) with the protein having immunological activity. Examples of adjuvants include cholera toxin, *salmonella* toxin, alum and such, but are not limited thereto. Furthermore, the vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

When using APC or CTL as the vaccine of this invention, tumors can be treated or prevented, for example, by the ex vivo method. More specifically, PBMCs of a subject receiving treatment or prevention therapy are collected, the cells are contacted with the polypeptide ex vivo, and following the induction of APC or CTL, the cells may be administered to the subject. APC can be also induced by introducing a vector encoding the polypeptide into PBMCs ex vivo. APC or CTL induced in vitro can be cloned prior to administration. By cloning and growing cells having high activity of damaging target cells, cellular immunotherapy can be performed more effectively. Furthermore, APC and CTL isolated in this manner may be used for cellular immunotherapy not only against individuals from whom the cells are derived, but also against similar types of tumors from other individuals.

Furthermore, a pharmaceutical composition for treating or preventing a cell proliferative disease, such as PRC, comprising a pharmaceutically effective amount of the ELOVL7 polypeptide is provided. The pharmaceutical composition may be used for raising anti tumor immunity. The normal expression of ELOVL7 is restricted to prostate. Therefore, suppression of this gene may not adversely affect other organs. Thus, the ELOVL7 polypeptides are preferable for treating cell proliferative disease, especially PRC. Furthermore, since peptide fragments of proteins specifically expressed in cancerous cells were revealed to induce immune response against the cancer, peptide fragments of ELOVL7 can also be used in a pharmaceutical composition for treating or preventing cell proliferative diseases such as PRC. In the present invention, the polypeptide or fragment thereof is administered at a dosage sufficient to induce anti-tumor immunity, which is in the range of 0.11 mg to 10 mg, preferably 0.3 mg to 5 mg, more preferably 0.8 mg to 1.5 mg. The administrations are repeated. For example, 1 mg of the peptide or fragment thereof may be administered 4 times in every two weeks for inducing the anti-tumor immunity.

In addition, polynucleotide encoding ELOVL7, or fragments thereof may be used for raising anti tumor immunity. Such polynucleotides may be incorporated in an expression vector to express ELOVL7, or fragments thereof in a subject to be treated. Thus, the present invention encompasses method for inducing anti tumor immunity wherein the polynucleotide encoding ELOVL7, or fragments thereof are administered to a subject suffering or being at risk of developing cell proliferative diseases such as PRC.

The following examples are presented to illustrate the present invention and to assist one of ordinary skill in making and using the same. The examples are not intended in any way to otherwise limit the scope of the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. Any patents, patent applications and publications cited herein are incorporated by reference.

BEST MODE FOR CARRYING OUT THE INVENTION

The present invention is illustrated in details by following Examples, but is not restricted to these Examples.

Cell Lines and Tissues.

Human PRC cell lines LNCaP, DU-145, 22Rv1, and PC-3 were obtained form American Type Culture Collection (ATCC, Rockville, Md.). All of the cells were cultured as monolayers in the following media: RPMI 1640 (Sigma-Aldrich, St. Louis, Mo.) for LNCaP and 22Rv1; and DMEM (Sigma-Aldrich) for DU-145; and F-12 (Invitrogen, Carlsbad, Calif.) for PC-3 with 10% fetal bovine serum and 1% antibiotic/antimycotic solution (Sigma-Aldrich). Cells were maintained in incubators containing humidified air with 5% $CO_2$ at 37° C. Frozen or paraffin-embedded PRC tissues were obtained from PRC patients who underwent radical prostatectomy with appropriate informed consent as described previously (Ashida S., et. al., Cancer Res 2004; 64:5963-72).

Semi-Quantitative RT-PCR.

Total RNA was extracted from cell lines, microdissected PRC cells, and bulk PRC tissues using TRIzol reagent (Invitrogen) according to manufacture's instruction. Extracted total RNA was treated with DNase I (Roche Diagnostic, Mannheim, Germany) and reversely transcribed to single-stranded cDNA using oligo d(T)$_{12-18}$ primer with Superscript reverse transcriptase II (Invitrogen). We prepared appropriate dilutions of each single-strand cDNA followed by normalizing cDNA content using β2-MG as a quantitative control, demonstrating PCR reaction using single strand cDNA as PCR templates. Primer sequences were the followings: β2-MG (forward: 5'-CACCCCCACTGAAAAAGAGA-3' (SEQ ID NO.1), reverse: 5'-TACCTGTGGAGCAAGGTGC-3' (SEQ ID NO.2)) and ELOVL7 (forward 5'-TCTAT-GAATCCTTGAGGGCCTA-3' (SEQ ID NO.3), reverse: 5'-TGACAACATCCACAGAATGTTCC-3' (SEQ ID NO.4)). The conditions for PCR are followed; initial denaturation at 95° C. for 5 min, 20 cycles for, β2-MG and 30 cycles for ELOVL7 of denaturation at 95° C. for 30 sec, annealing at 55° C. for 30 sec, and elongation at 72° C. for 30 sec on a GeneAmp PCR system 9700 (PE Applied Biosystems, Foster, Calif.).

Northern Blotting Analysis.

Human multiple-tissue blots (BD Bioscience, Palo Alto, Calif.) were hybridized for 20 hours with $^{32}$P-labeled ELOVL7 cDNA, which was labeled using a Mega Label kit (Amersham, Piscataway, N.J.). Probe cDNA of ELOVL7 was prepared as a 785-bp PCR product by using the primers followings: ELOVL7 (forward 5'-AGAGCACAGCTAAAT-GAAACTGC-3' (SEQ ID NO.5), reverse: 5'-TGACAA-CATCCACAGAATGTTCC-3' (SEQ ID NO.6)). Pre-hybridization, hybridization, and washing were performed according to the manufacture's instruction. The blots were autoradiographed at –80° C. for 7 days.

Generating Antibody to ELOVL7 and Immunohistochemical Analysis.

The N-terminal peptide (SDLTSRTVHLYDNWIKDA) (SEQ ID NO. 16) and C-terminal peptide (CHFWYRAYT-KGQRLPKTVK) (SEQ ID NO. 17) of ELOVL7 were generated by MBL (Nagoya, Japan) and are immunized to rabbits. Serum from the immunized rabbits was purified these peptides. Paraffin-embedded tissue sections were deparaffinized, subjected to treatment with microwave at 600 W for 1 min 4 times in antigen retrieval solution, high pH (DAKO, Carpinteria, Calif.), and then treated with peroxidase blocking reagent (DAKO) followed by protein block reagent (DAKO). Tissue sections were incubated with a polyclonal antibody against ELOVL7 followed by horseradish peroxidase-conjugated secondary antibody (DAKO). Antigen was visualized with diaminobensidine (DAKO) staining and sections were counterstained with hematoxylin.

Construction of siRNA Expressing Vectors and Cell Viability Assay.

To investigate the biological function of ELOVL7 in PRC cells, we used psiU6BX3.0 vector for expression of short hairpin RNA against a target gene as described previously (Anazawa Y, et al., Cancer Res. 2005; 65:4578-86). Plasmids designed to express siRNA were prepared by cloning of double-stranded oligonucleotides into psiU6BX vector. The oligonucleotide sequences of target sequences for ELOVL7 are as followed; sense strand sequence for si#5: 5'-CAAG-CAACAACAACAACAA-3' (SEQ ID NO.7) and siEGFP: 5'-GAAGCAGCACGACTTCTTC-3' (SEQ ID NO. 1) as a negative control. PRC cell lines LNCaP and 22Rv1 cells ($2\times10^6$), which expressed ELOVL7 in high level, were grown on 10-cm dishes, transfected with psiU6-ELOVL7 (si#5), or psiU6-siEGFP using FuGene6 reagent (Roche) according to supplier's protocol, and then cultured in appropriate medium containing 800 μg/ml of Geneticin for 2 weeks. The cells were fixed with 100% methanol, stained with 0.1% of crystal violet-$H_2O$ for colony formation assay. In MTT assay, cell viability was measured using Cell-counting kit-8 (DOJINDO, Kumamoto, Japan) at 10 days after transfection. Absorbance was measured at 490 nm, and at 630 nm as reference, with a Microplate Reader 550 (Bio-Rad). Preliminarily, knockdown effects of these siRNA expression vectors on endogenous ELOVL7 expression were validated 7 days after transfection by RT-PCR using the primers described earlier.

Oligonucleotide sequences used for small interfering RNA of ELOVL7 are shown below.

TABLE 1

| | | SEQ ID NO | sequence | | | position |
|---|---|---|---|---|---|---|
| ELOVL7 | target | 7 | caagcaacaa | caacaacaa | | 3531-3549 |
| si#5 | insert seq | 8 | cacccaagca gattgttgtt | acaacaacaa gttgttgctt | caattcaaga g | |
| | | 9 | aaaacaagca aattgttgtt | acaacaacaa gttgttgctt | caatctcttg g | |
| | hairpin | 10 | caagcaacaa gttgttgttg | caacaacaat ttgcttg | tcaagagatt | |
| EGFP (control) | target insert seq | 11 | gaagcagcac | gacttcttc | | |
| | | 12 | caccgaagca gagaagaagt | gcacgacttc cgtgctgctt | ttcttcaaga c | |
| | | 13 | aaaagaagca aagaagaagt | gcacgacttc cgtgctgctt | ttctctcttg c | |

Fatty Acid Analysis in Cells with ELOVL7 Knocked Down.

LNCaP cells were transfected with siRNA-expression vector (si5 or control siEGFP) and incubated with Geneticin for 7 days. Preliminary, we validated knockdown effect on ELOVL7 expression and cell viability or active cell numbers were not affected at day 7. At day 7 the lipid was extracted from the cells by Folch liquid (methanol:chloroform 1:2, vol:vol), and evaporated under nitrogen gas. After hydration by 0.5 M HCl, free fatty acid was extracted by chloroform and methyl-esterized by 0.4 K methoxide/methanol and 14% boron trifluoride methanol. Each fatty acid level in the cells was subject to gas chromatography mass spectrometry (GC-17A, Shimazu, Kyoto, Japan).

Expression of Recombinant Protein in Insect Cells.

Recombinant baculovirus expressing ELOVL7 was generated using the BacPAK baculovirus expression system (Clontech) according to the manufacture's instructions. Full-length ELOVL7 cDNA (Genbank accession no. NM_024930) was PCR amplified using following primers that were designed to contain 6×His-tag sequences at the NH2 terminus, and cloned into the pBacPAK 9 vector. A forward primer for ELOVL7 is 5'-CCCCTGGGATCCACCATGGGTCATCAT-CATCACCATCACGAATTCGCCTTCAGT-GATCTTACATCG-3' (SEQ ID NO: 18) and a revers primer for ELOVL7 is 5'-CCGCTCGAGTCAAT-TATCTTTGTTTTTGCAAGTTCC-3' (SEQ ID NO: 19). Spodoptera frugiperda (Sf21) cells were cultured in Grace's insect medium (GIBCO) supplemented with 10% fetal bovine serum and 50 µg/ml gentamycin (Sigma-Aldrich) at 27° C. and infected with the indicated recombinant baculovirus. 72 hours after infection, the cells were collected and washed once with PBS. The microsomes were isolated by differential centrifugation with modifications to the procedure described by Moon et al (Moon Y A, et al. J Biol Chem. 2001; 276:45358-45366.). Briefly, the cells were suspended in 0.25 M sucrose, 10 mM Tris-Cl (pH7.4), 1 mM EDTA, and 0.1% protease inhibitor cocktail III (Calbiochem, San Diego, Calif.) and disrupted using a Microson ultrasonic cell disruptor. Cell homogenates were centrifuged at 5,000 rpm for 10 min at 4° C., the supernatant was collected and centrifuged at 15,000 rpm, for 20 min at 4° C. The resulting supernatant was then centrifuged at 55,000 rpm for 30 min at 4° C. in a Beckman TLA 100.2 rotor, and the pellets were suspended in a buffer that contained 50 mM Tris-Cl (pH7.4), 1 mM EDTA, 20% glycerol and the protease inhibitor cocktail III described above. Aliquots of the microsomes were stored at −80° C. after quick freezing in liquid nitrogen and were used for western blotting analysis and in vitro fatty acid elongation assay.

Western Blotting Analysis.

The microsomal proteins were denatured in SDS sample buffer at 4° C. overnight to prevent protein aggregations. 30 µg each of SDS sample was loaded onto 15% SDS-PAGE gel and blotted onto nitrocellulose membranes. Protein bands were visualized by chemiluminescent detection system (ECL, Amersham).

In Vitro Fatty Acid Elongation Assay.

Fatty acid elongation activity was measured in microsomes prepared from baculoviral infected Sf21 cells described above. Reaction mixtures contained 10~200 µg of microsomes in a total reaction volume of 0.45 ml. The reaction constituents were 0.1 M Tris-Cl (pH 7.4), 3 mM Arachidoyl-CoA, 7.5 mM Malonyl-CoA, 20 mM NADPH, and 0.6 mM fatty acid-free BSA (Sigma-Aldrich). The vapor phase in a glass tube of reaction mixtures was substituted by nitrogen gas on ice for 5 min and then injected microsomes into glass tubes using a syringe. The reaction incubated at 37° C. for 5 min and stopped with Folch liquid (methanol:chloroform 1:2, vol:vol). Each fatty acid level in the reaction samples was analyzed using gas chromatography mass spectrometry described above.

Results

Identification of a Novel Gene, ELOVL7, and its Expression Pattern.

Figure 2:
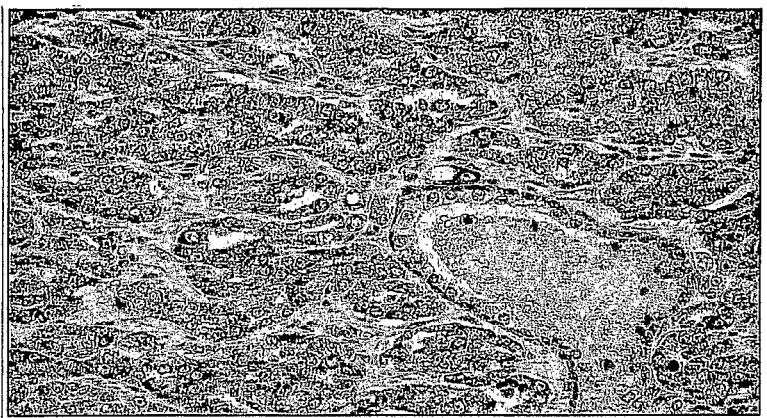
FIG. 2 shows Immunohistochemical analysis of PRC tissues by anti-ELOVL7 antibody. Immunoreactivity with anti-ELOVL7 antibody was observed in PRC tissues examined, exhibiting strong positive immunostaining in cytoplasm of PRC cells (A) and, whereas very week cytoplasmic immunopositivity was observed in PIN precursors of PRC (B), and non-cancerous prostate epithelium (C). Representative data from immunohistochemical studies of twelve PRC specimens are shown.
Figure 2:
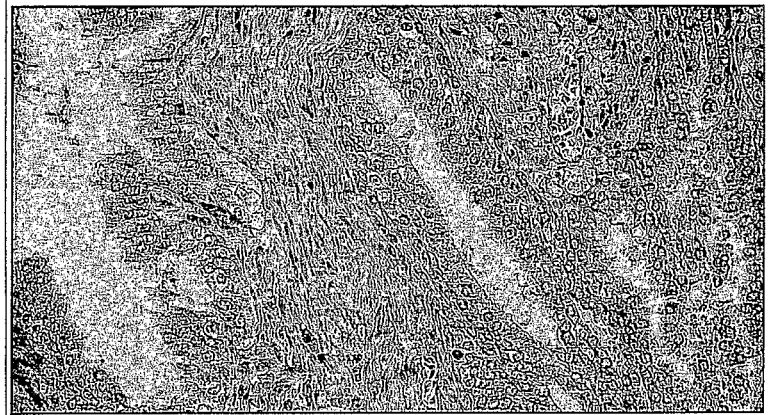
Figure 2:
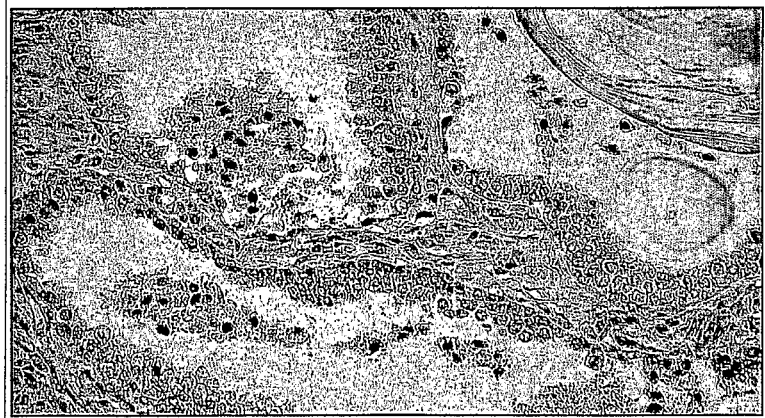

We previously reported the genome-wide expression profiles of PRC cells and PINs purified from clinical PRC tissues by means of cDNA microarray analysis representing 27,000 genes in combination with the LMM system (Ashida S., et. al., Cancer Res 2004; 64:5963-72). Among a number of genes shown to be trans-activated in PRC cells and/or PIN cells compared with normal prostate epithelial cells, we focused on ELOVL7 in this report. Semi-quantitative RT-PCR confirmed the elevated expression of ELOVL7 in PRC cells in 8 of the 12 clinical PRC samples, comparing to that of normal prostate epithelium, as shown in FIG. 1A. Northern blot analysis to investigate the tissue distribution of ELOVL7 identified an approximately 3.8 kb ELOVL7 transcript in prostate, kidney, and other several tissues (FIG. 1B), but RT-PCR analysis (FIG. 1C) demonstrated that ELOVL7 expression in PRC cells were obviously higher than that of normal kidney or prostate, implicating its distinct expression in PRC cells. To further investigate the expression of ELOVL7 protein in PRC cells, we generated polyclonal antibody to ELOVL7 by immunizing its N-terminal or C-terminal peptides and performed immunohistochemical analysis. As shown in FIG. 2A, strong immunochemical signal for ELOVL7 was detected predominantly in the cytoplasm of PRC cells in all of twelve PRC cases examined, although we observed a weak signal in non-cancerous prostate epithelial cells and PINs (FIGS. 2B, C) as concordant to the results of multiple tissue northern blot analysis. All of the twelve PRCs we examined showed strong immunoreactivity to anti-ELOVL7 antibody.

Knockdown of ELOVL 7 Expression Attenuated Prostate Cancer Cell Growth.

Figure 3:
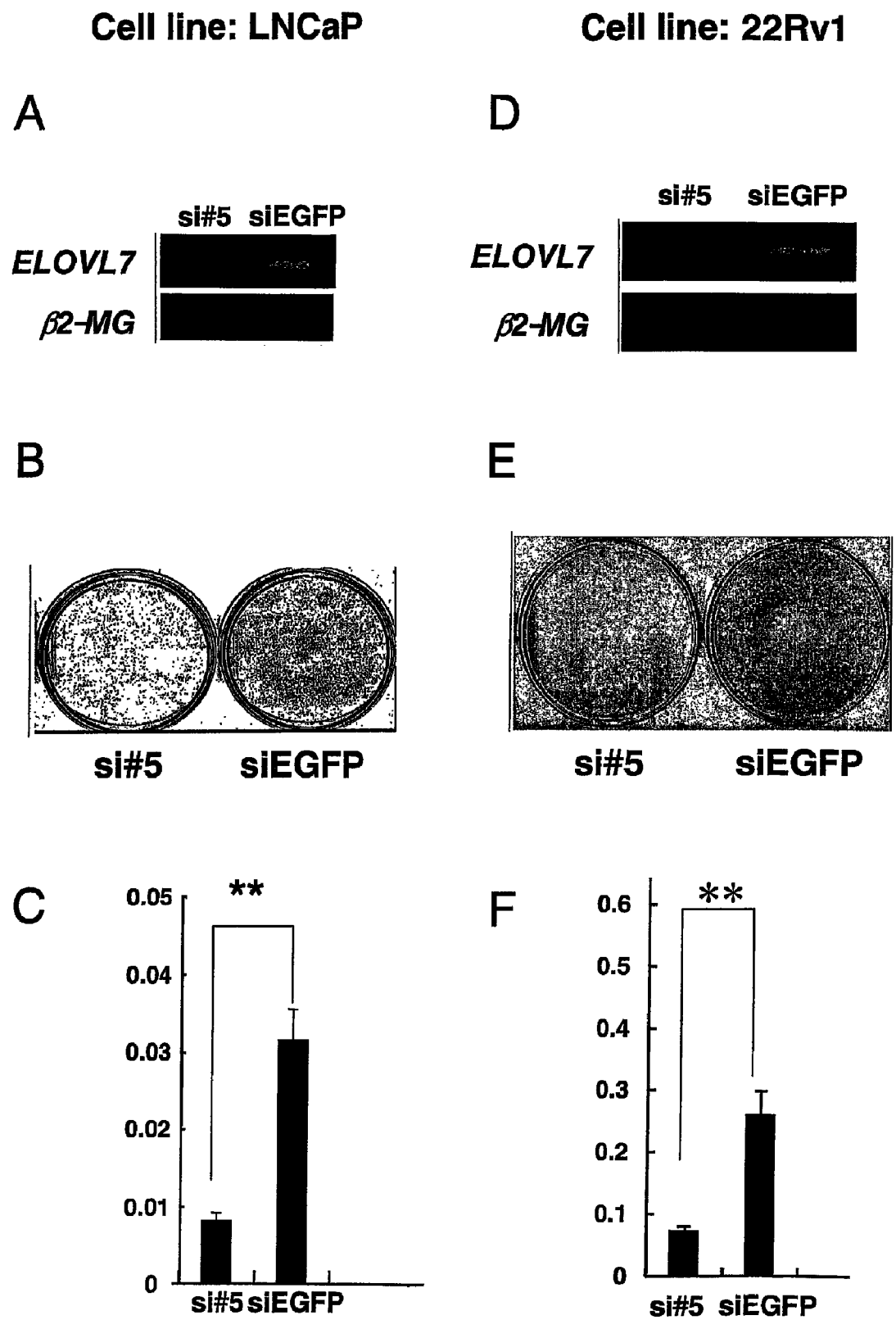
FIG. 3 shows Knockdown of ELOVL7 expression by siRNA in LNCaP and 22Rv1 cells caused attenuation of PRC cell growth and cell viability.

To examine roles of ELOVL7 expression in PRC cell growth, we constructed several expression vectors designed to express siRNA specifically to ELOVL7, and transfected them into PRC cell lines LNCaP and 22Rv1, which expressed ELOVL7 endogenously. Among the five plasmids we tested in LNCaP cells, ELOVL7-si#5 showed the significant knockdown effect on endogenous ELOVL7 transcript (FIG. 3A), and this transfection resulted in reduction of the numbers of colonies (FIG. 3B) as well as those of the viable cells measured by MTT assay for LNCaP cells (FIG. 3C), while a negative control (siEGFP) showed little knockdown effect on ELOVL7 expression and did not affect cell viability of LNCaP. The similar findings were obtained on another PRC cell line, 22Rv1 cells, as shown in FIGS. 3D, E and F.

Change of Fatty Acid Fraction by Knockdown of ELOVL7.

Figure 4:
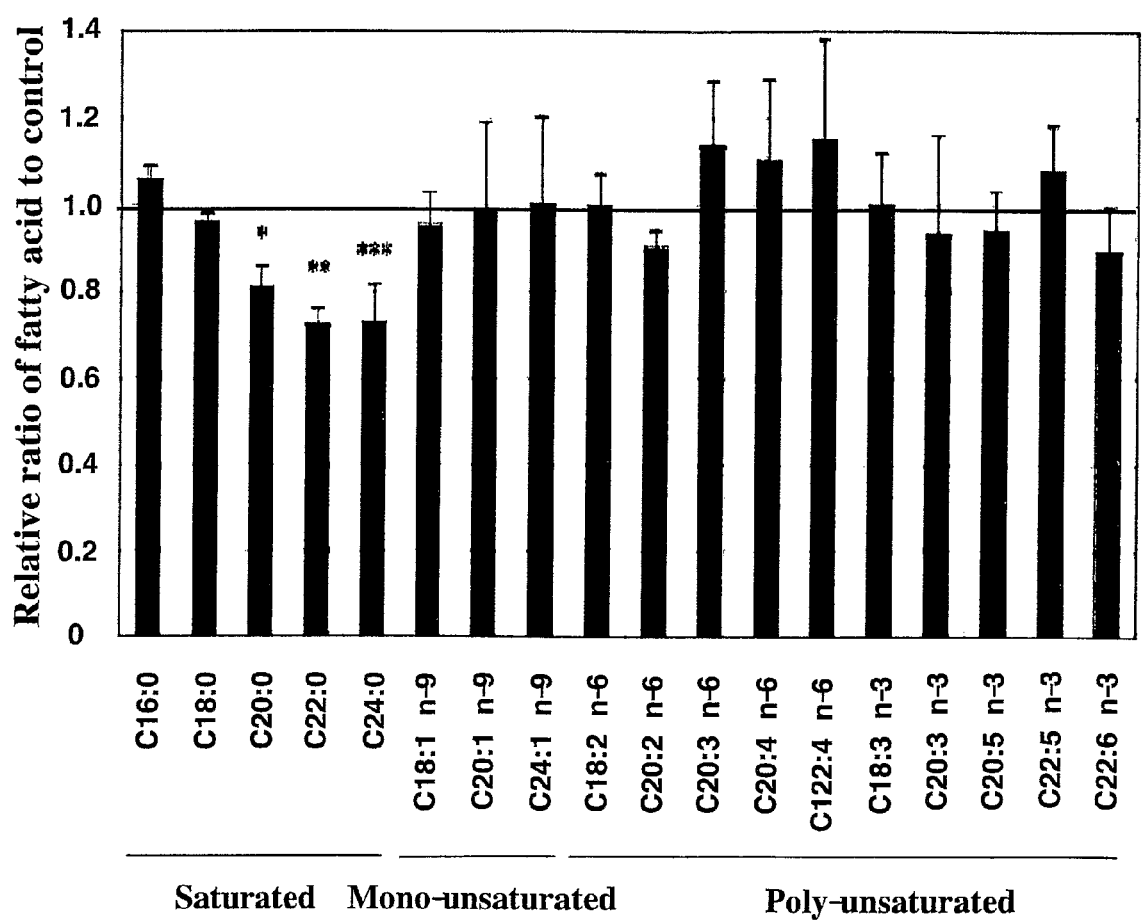
FIG. 4 Change of fatty acid fraction by knockdown of ELOVL7. At day 7 after the transfection of ELOVL7-si5 or control siRNA into LNCaP cells, the lipids were extracted from them and subject to analysis of fatty-acid fraction by gas chromatography. ELOVL7-si5 transfection showed the significant reduction (20-30%) of long-chain saturated fatty acid level (C20:0 p=0.002, C22:0 p=0.008, C24:0 p=0.003) compared with siEGFP transfection, while ELOVL7-si5 transfection did not affect the levels of mono-unsaturated fatty acids (n-9) and poly-unsaturated fatty acids (n-6 and n-3) in the PC cells.

Next we examined the effects on fatty acid synthesis by knockdown of ELOVL7 expression. We transfected ELOVL7-si5 that confirmed its significant knockdown effect on ELOVL7 or siEGFP as a negative control to LNCaP cells. At day 7 after the transfection, when ELOVL7 expression was apparently knocked down but the cell viability of the siELOVL7-transfected cells were not significantly affected, comparing to that of siEGFP-transfected cells, we harvested the cells and analyzed their fatty-acid fraction by gas chromatography. ELOVL7-si5 transfection showed the significant reduction (20-30%) of long- and very-long-chain saturated fatty acid level (C20:0 p=0.02, C22:0 p=0.008, C24:0 p=0.003) compared with siEGFP transfection (FIG. 4), while ELOVL7-si5 transfection showed no effect of monounsaturated fatty acid and polyunsaturated fatty acid level. These findings indicated that ELOVL7 could be involved preferentially in elongation activity of monounsaturated long-chain fatty acid.

In Vitro Fatty-Acid Elongation Assay.

Figure 5:
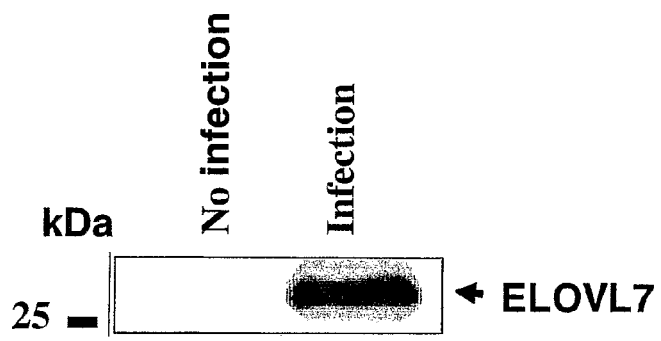
FIG. 5 Expression of human recombinant ELOVL7 protein and its fatty acid elongase activity in vitro. (A) The 30 μg microsomal proteins from the infected or non-infected insect cells were loaded onto 15% SDS-PAGE gel and Western blotting analysis with 1:1000 dilution of an anti-His antibody detected 30-kDa recombinant human ELOVL7 in the microsomes of the infected insect cells. (B) In vitro fatty acid elongation activity using the 50 μg microsomes from the infected insect cells. The increments of each fatty acid level before and after the 5-min reaction were shown, and the microsome from the infected cells yielded C22:0 and C24:0 significantly, while the control microsome yielded C20:0 but not C22:0 and C24:0 at all. C20:0 production by the control microsome is likely to be due to the endogenous fatty acid elongation activity of Sf21 insect cells, and in the microsome including human ELOVL7 protein, the elongation reactions from C20:0 to C22:0, C24:0 or more could proceed actively, resulting in less yielding of C20:0. (C) Fatty-acid chain elongation activity was dependent on the dose of the enzyme source, the microsomes of the infected cells. The reaction mixtures contained 10~200 μg of microsomes in a total reaction volume of 0.45 ml. The reaction constituents were 0.1 M Tris-Cl (pH 7.4), 3 mM Arachidoyl-CoA, 7.5 mM Malonyl-CoA, 20 mM NADPH, and 0.6 mM fatty acid-free BSA. Similar results were obtained in three independent experiments.
Figure 5:
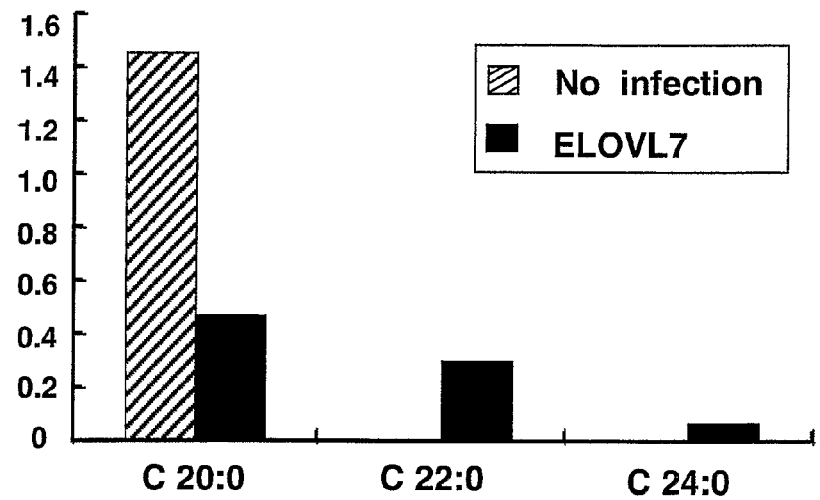
Figure 5:
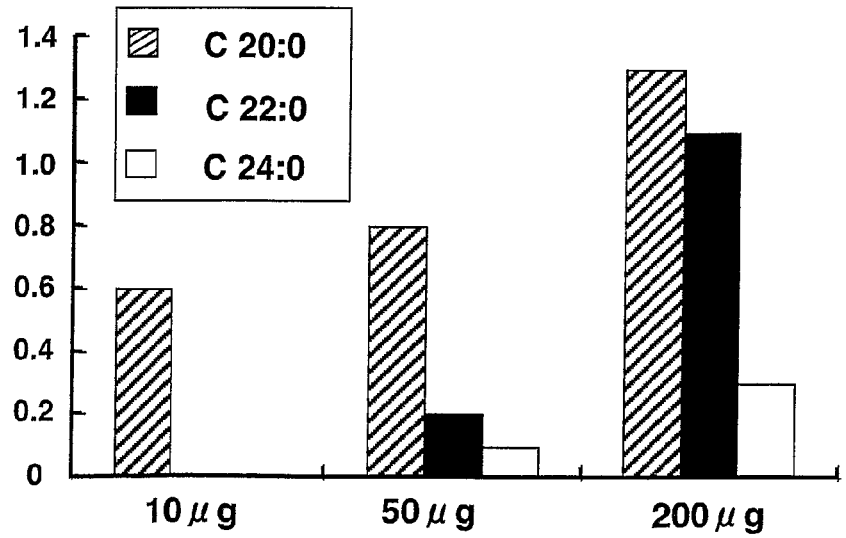

To examine more detailed about the actual activity of ELOVL7 as a fatty acid elongase, recombinant ELOVL7 protein was generated using the BacPAK baculovirus expression system. This recombinant baculovirus produced protein of approximately 30 kDa, and western blotting analysis with anti-His monoclonal antibody revealed that the expressed ELOVL7 protein was present in the microsome of cells (FIG. 5A). We adapted the microsome fraction of the insect cell transfected with ELOVL7-expression virus or non-transfected cells for an enzyme source of the fatty acid elongation assay in vitro. Elongation activity was measured as increment of each fatty acid level before and after the 5-min reaction. Initially, stearoyl-CoA (C18:0) was empirically chosen as the substrates in the elongation assay from the result of siRNA experiments described above. However, it was found that half of fatty acids in microsomes contained stearic acid (C18:0), which masked the difference of fatty-acid fraction. Therefore, arachidoyl-CoA (C20:0) was used as the substrate. FIG. 5B showed the increment of each fatty acid level before and after the 5-min reaction, and the microsome from the infected cells yielded some C22:0 and C24:0, while the control microsome yielded C20:0 but not C22:0 and C24:0 at all. C20:0 production by the control microsome is likely to be due to the endogenous fatty acid elongation activity of Sf21 insect cells, and in the microsome including human ELOVL7 protein, the elongation from C20:0 to C22:0, C24:0 or more could proceed actively, resulting in less yielding of C20:0 (FIG. 5B). Moreover, this fatty-acid chain elongation activity was dependent on the dose of the enzyme source, the microsomes of the infected cells (FIG. 5C). These data suggested that ELOVL7 in the microsome showed actual activity of fatty-acid elongase yielding C22:0 and C24:0.

Discussions

In the present invention, we focused on a novel gene, ELOVL7, as one of the trans-activated genes in PRC cells. Northern blot analysis showed that ELOVL7 was expressed in prostate and kidney, but RT-PCR analysis revealed that ELOVL7 expression of PRC cells was apparently higher than that of normal kidney and other vital organs. These findings of ELOVL7 expression implicated its distinct expression in PRC cells and its possibility of favor molecular targets, considering that molecular targeting to ELOVL7 for a novel therapeutic approach with minimal side effect of vital organs. Our immunohistochemical study using polyclonal antibody to ELOVL7 also clearly indicated up-regulation of ELOVL7 expression in PRC cells also.

There are six ELOVL family members (ELOVL1-6) in mammalian reported so far and some of them show tissue-specific expression or use specific fatty acid substrates. According to our genome-wide gene expression data of PRC and other organs (Ashida S., et. al., Cancer Res 2004; 64:5963-72) ELOVL7 is expressed at the highest level in prostate and PRC cells among seven ELOVL family member (ELOVL1-7). These findings for ELOVL expression pattern can lead to the speculation that ELOVL7 is likely to function specifically in prostate and PRC and involve some specific pathway in prostate out of diverse metabolic pathways of long-chain fatty acids. Thus identification of specific substrates or pathways involved by ELOVL7 in prostate or PRC should be further investigated.

In a number of epidemiological studies, it is apparent that taking high fat diet is strongly associated with prostate carcinogenesis (Kolonel L N, et. al., J. Natl. Cancer Inst. 1999; 91:414-28, Schulman C C, et. al., Urology. 2001; 58:318-34). In our previous microarray study, several genes associated with lipid or cholesterol metabolism were up-regulated in prostate cancer and its precursor PINs (Ashida S, et. al., Cancer Res. 2004; 64:5963-72.), and there are a number of evidences that lipid or cholesterol metabolism and the lipid metabolism-associated genes are likely to play some important roles of PRC development and progression through its metabolic pathway or anti-apoptotic effect (De Schrijver E, et. al., Cancer Res. 2003; 63: 3799-804., Baron A, et. al., J. Cell Biochem. 2004; 91: 47-53.). Among them, fatty acid synthase (FAS), enzyme responsible for synthesis of palmitate, that is the precursor of long-chain nonessential fatty acids, was reported to be up-regulated in a wide range of cancers and has been suggested as a relevant drug target (De Schrijver E, et. al., Cancer Res. 2003; 63: 3799-804., Baron A, et. al., J. Cell Biochem. 2004; 91: 47-53.). Furthermore, cholesterol elevation itself can promote PRC cell proliferation and some cholesterol synthesis inhibitors are now expected to be promising drugs for cancer prevention or treatment (Zhuang L, et. al., J. Clin. Invest. 2005; 115: 959-68.). In the similar way with cholesterol, long-chain fatty acids abundant in high fat diet can be involved in PRC proliferation through membrane stabilization, cell signaling pathways, and other unknown functions. Our functional analysis using siRNA to ELOVL7 demonstrated that ELOVL7 expression was essential to PRC proliferation or prostate tumorigenesis, and targeting directly to ELOVL7 enzyme function or the pathway of long-chain fatty acids involved by ELOVL7 in PRCs is thought to be a promising approach for a novel therapeutic or preventive strategies against PRCs.

Our fatty acid analysis in vivo and in vitro suggested that, among the diverse lipid metabolism, ELOVL7 was involved in the elongation or synthesis of saturated long or very long-chain fatty acids (SLFAs), rather than poly-unsaturated fatty acids that are known to have promoting or suppressing effect on cancer development (De Schrijver E, et al. Cancer Res. 2003; 63: 3799-804.; Baron A., et al. J. Cell Biochem. 2004; 91: 47-53.; Diggle C P. Prog Lipid Res. 2002; 41; 240-53.). SLFAs are very abundantly contained in animal meat as well as cholesterol and they can also be thought to be strongly associated with risk of prostate cancer development, according to the epidemiological or nutritional studies (Kolonel L N, et al. J Natl Cancer Inst. 1999; 91:414-28.; Schulman C C, et al. Urology 2001; 58: 318-34.) and indeed SLFAs were more abundant in invasive prostate cancer tissues (Freeman V L, et al. J Urol 2000; 164: 2168-72.). However, it remains unclear how SLFAs can involve carcinogenesis or cancer progression. SLFAs, as well as cholesterol, compose the lipid raft of the plasma membrane, where a variety of signal transduction proteins can partition and function actively (Zhuang L, et al. J Clin Invest 2005; 115: 959-68.; Pike L J. J Lipid Res 2003; 44: 655-67.), and SLFAs yielded by ELOVL7 in PC cells may promote the quality and quantity of the lipid raft platform for growth or anti-apoptotic signaling. Our functional analysis using siRNA to ELOVL7 demonstrated that ELOVL7 expression was essential to prostate cancer proliferation or prostate tumorigenesis, and targeting directly to ELOVL7 enzyme function or the pathway of SLFAs involved by ELOVL7 in prostate cancers is thought to be a promising approach for a novel therapeutic or preventive strategies against prostate cancers.

Summarily, saturated long-chain fatty acid metabolism by ELOVL7 can be essential in PRC growth or development, although the detail pathways or substrates involved by ELOVL7 remains unknown, and the inhibition of ELOVL7 may provide us a novel promising approach for molecular treatment or prevention of PRC.

INDUSTRIAL APPLICABILITY

The expression of human genes ELOVL7 is markedly elevated in PRC as compared to non-cancerous prostate epithelium. Accordingly, this gene is useful as a diagnostic marker of PRC and the proteins encoded thereby are useful in diagnostic assays of PRC.

The present inventors have also shown that the expression of novel protein ELOVL7 promotes cell growth whereas cell growth is suppressed by small interfering RNAs corresponding to the ELOVL7 gene. These findings show that ELOVL7 protein stimulates oncogenic activity. Thus, each of these novel oncoproteins is a useful target for the development of anti-cancer pharmaceuticals. For example, agents that block the expression of ELOVL7, or prevent its activity find therapeutic utility as anti-cancer agents, particularly anti-cancer agents for the treatment of PRC. Examples of such agents include antisense oligonucleotides, small interfering RNAs, and ribozymes against the ELOVL7 gene, and antibodies that recognize ELOVL7.

While the invention has been described in detail and with reference to specific embodiments thereof, it will be apparent to one skilled in the art that various changes and modifications can be made therein without departing from the spirit and scope of the invention.

The invention claimed is:

1. A method of screening for a compound for treating or preventing prostate cancer, said method comprising the steps of:
   (a) contacting a test compound with a polypeptide selected from the group consisting of:
      (1) a polypeptide comprising the amino acid sequence of SEQ ID NO: 15; and
      (2) a polypeptide that comprises the amino acid sequence of SEQ ID NO: 15 or a sequence having at least 99% identity to SEQ ID NO: 15, wherein the polypeptide has a fatty acid elongation activity;
   (b) detecting the fatty acid elongation activity of the polypeptide of step (a);
   (c) selecting a compound that suppresses the fatty acid elongation activity of the polypeptide in comparison with the fatty acid elongation activity detected in the absence of the test compound to isolate a candidate compound for treating or preventing prostate cancer; and
   (d) detecting the ability of the compound isolated in step (c) to treat or prevent prostate cancer.

* * * * *

SEQUENCE LISTING

```
<160> NUMBER OF SEQ ID NOS: 19

<210> SEQ ID NO 1
<211> LENGTH: 20
<212> TYPE: DNA
<213> ORGANISM: Artificial
<220> FEATURE:
<223> OTHER INFORMATION: Artificially synthesized primer for RT-PCR

<400> SEQUENCE: 1 caccccact gaaaagaga                                                  20

<210> SEQ ID NO 2
<211> LENGTH: 19
<212> TYPE: DNA
<213> ORGANISM: Artificial
<220> FEATURE:
<223> OTHER INFORMATION: Artificially synthesized primer for RT-PCR

<400> SEQUENCE: 2
tacctgtgga gcaaggtgc                                                 19

<210> SEQ ID NO 3
<211> LENGTH: 22
<212> TYPE: DNA
<213> ORGANISM: Artificial
<220> FEATURE:
<223> OTHER INFORMATION: Artificially synthesized primer for RT-PCR

<400> SEQUENCE: 3
```
tctatgaatc cttgagggcc ta                                                  22

<210> SEQ ID NO 4
<211> LENGTH: 23
<212> TYPE: DNA
<213> ORGANISM: Artificial
<220> FEATURE:
<223> OTHER INFORMATION: Artificially synthesized primer for RT-PCR

<400> SEQUENCE: 4
tgacaacatc cacagaatgt tcc                                                 23

<210> SEQ ID NO 5
<211> LENGTH: 23
<212> TYPE: DNA
<213> ORGANISM: Artificial
<220> FEATURE:
<223> OTHER INFORMATION: Artificially synthesized primer for RT-PCR

<400> SEQUENCE: 5
agagcacagc taaatgaaac tgc                                                 23

<210> SEQ ID NO 6
<211> LENGTH: 23
<212> TYPE: DNA
<213> ORGANISM: Artificial
<220> FEATURE:
<223> OTHER INFORMATION: Artificially synthesized primer for RT-PCR

<400> SEQUENCE: 6
tgacaacatc cacagaatgt tcc                                                 23

<210> SEQ ID NO 7
<211> LENGTH: 19
<212> TYPE: DNA
<213> ORGANISM: Artificial
<220> FEATURE:
<223> OTHER INFORMATION: Artificially synthesized target sequence for
      siRNA

<400> SEQUENCE: 7
caagcaacaa caacaacaa                                                      19

<210> SEQ ID NO 8
<211> LENGTH: 51
<212> TYPE: DNA
<213> ORGANISM: Artificial
<220> FEATURE:
<223> OTHER INFORMATION: Artificially synthesized oligonucleotide for
      siRNA

<400> SEQUENCE: 8
cacccaagca acaacaacaa caattcaaga gattgttgtt gttgttgctt g                  51

<210> SEQ ID NO 9
<211> LENGTH: 51
<212> TYPE: DNA
<213> ORGANISM: Artificial
<220> FEATURE:
<223> OTHER INFORMATION: Artificially synthesized oligonucleotide for
      siRNA

<400> SEQUENCE: 9
aaaacaagca acaacaacaa caatctcttg aattgttgtt gttgttgctt g                  51

<210> SEQ ID NO 10
<211> LENGTH: 47

```
<212> TYPE: DNA
<213> ORGANISM: Artificial
<220> FEATURE:
<223> OTHER INFORMATION: si RNA hairpin design

<400> SEQUENCE: 10
caagcaacaa caacaacaat tcaagagatt gttgttgttg ttgcttg                         47

<210> SEQ ID NO 11
<211> LENGTH: 19
<212> TYPE: DNA
<213> ORGANISM: Artificial
<220> FEATURE:
<223> OTHER INFORMATION: Artificially synthesized target sequence for
      siRNA

<400> SEQUENCE: 11
gaagcagcac gacttcttc                                                       19

<210> SEQ ID NO 12
<211> LENGTH: 51
<212> TYPE: DNA
<213> ORGANISM: Artificial
<220> FEATURE:
<223> OTHER INFORMATION: Artificially synthesized oligonucleotide for
      siRNA

<400> SEQUENCE: 12
caccgaagca gcacgacttc ttcttcaaga gagaagaagt cgtgctgctt c                   51

<210> SEQ ID NO 13
<211> LENGTH: 51
<212> TYPE: DNA
<213> ORGANISM: Artificial
<220> FEATURE:
<223> OTHER INFORMATION: Artificially synthesized oligonucleotide for
      siRNA

<400> SEQUENCE: 13
aaaagaagca gcacgacttc ttctctcttg aagaagaagt cgtgctgctt c                   51

<210> SEQ ID NO 14
<211> LENGTH: 3815
<212> TYPE: DNA
<213> ORGANISM: Homo sapiens
<220> FEATURE:
<221> NAME/KEY: CDS
<222> LOCATION: (142)..(987)

<400> SEQUENCE: 14
cagtcgccgc cctctctccc gcgcgcgccc ggcgcttcgg ctccgctccc tgtgcggcat          60
ttaaacttcc ctcttagaac tgcttttgtg gcatcccata agttttgaac ccattaaaag         120
agccagtaaa tcctgtggaa a atg gcc ttc agt gat ctt aca tcg agg act           171
                       Met Ala Phe Ser Asp Leu Thr Ser Arg Thr
                         1               5                  10 gtg cat ctt tat gat aat tgg atc aaa gat gct gat cca aga gtt gaa          219
Val His Leu Tyr Asp Asn Trp Ile Lys Asp Ala Asp Pro Arg Val Glu
             15                  20                  25 gat tgg ctc ctc atg tcc tcg cct ctg cca caa acc atc ctc cta gga          267
Asp Trp Leu Leu Met Ser Ser Pro Leu Pro Gln Thr Ile Leu Leu Gly
         30                  35                  40 ttc tat gtc tat ttt gtc act tcc ttg gga cca aag ctc atg gaa aat          315
Phe Tyr Val Tyr Phe Val Thr Ser Leu Gly Pro Lys Leu Met Glu Asn
     45                  50                  55 cgc aag ccc ttt gaa ctc aag aaa gca atg ata acg tac aat ttt ttc          363
```

```
            Arg Lys Pro Phe Glu Leu Lys Lys Ala Met Ile Thr Tyr Asn Phe Phe
                 60              65                  70 ata gta ctc ttt tct gtg tat atg tgt tat gag ttt gtg atg tct ggc        411
Ile Val Leu Phe Ser Val Tyr Met Cys Tyr Glu Phe Val Met Ser Gly
 75              80              85                  90 tgg ggt ata ggt tat tca ttt cga tgt gac att gtt gac tat tca cgg        459
Trp Gly Ile Gly Tyr Ser Phe Arg Cys Asp Ile Val Asp Tyr Ser Arg
                 95              100             105 tca ccc aca gct ttg agg atg gca cgt acc tgc tgg ctt tat tac ttc        507
Ser Pro Thr Ala Leu Arg Met Ala Arg Thr Cys Trp Leu Tyr Tyr Phe
             110             115                 120 tcc aaa ttt att gag cta tta gat acg atc ttt ttt gtt ctg cgc aag        555
Ser Lys Phe Ile Glu Leu Leu Asp Thr Ile Phe Phe Val Leu Arg Lys
             125             130                 135 aaa aat agc caa gtg act ttc ctt cat gta ttc cat cat acc atc atg        603
Lys Asn Ser Gln Val Thr Phe Leu His Val Phe His His Thr Ile Met
     140             145                 150 ccg tgg acc tgg tgg ttt gga gtc aaa ttt gct gca ggt ggt ttg gga        651
Pro Trp Thr Trp Trp Phe Gly Val Lys Phe Ala Ala Gly Gly Leu Gly
155             160                 165                 170 aca ttc cat gcc ctt cta aat aca gct gta cat gta gtc atg tat tcc        699
Thr Phe His Ala Leu Leu Asn Thr Ala Val His Val Val Met Tyr Ser
                 175             180             185 tac tat gga ctt tct gca ttg ggg cca gcc tac cag aag tat ttg tgg        747
Tyr Tyr Gly Leu Ser Ala Leu Gly Pro Ala Tyr Gln Lys Tyr Leu Trp
             190             195                 200 tgg aaa aaa tat ttg aca tca tta cag ctt gtc cag ttt gtt att gtc        795
Trp Lys Lys Tyr Leu Thr Ser Leu Gln Leu Val Gln Phe Val Ile Val
             205             210                 215 gcc atc cac ata agc cag ttc ttt ttc atg gag gat tgc aag tat cag        843
Ala Ile His Ile Ser Gln Phe Phe Phe Met Glu Asp Cys Lys Tyr Gln
 220             225                 230 ttt cca gtc ttt gcg tgc atc att atg agt tac agt ttc atg ttt ccg        891
Phe Pro Val Phe Ala Cys Ile Ile Met Ser Tyr Ser Phe Met Phe Pro
235             240                 245                 250 ctg ctc ttt ctc cat ttt tgg tac cgt gct tac acc aaa ggt cag agg        939
Leu Leu Phe Leu His Phe Trp Tyr Arg Ala Tyr Thr Lys Gly Gln Arg
                 255             260                 265 ttg ccc aaa act gtg aaa aat gga act tgc aaa aac aaa gat aat tga        987
Leu Pro Lys Thr Val Lys Asn Gly Thr Cys Lys Asn Lys Asp Asn
             270             275                 280 agcccaacat aagtctatga tcgaaactga tacattgtct tccttgacaa tcaagagata     1047
tttacctatg cagtgcattt tgtatatttt tcaaaactaa gagcttgtat ttttatggta     1107
agttattggg atgtctgata tttgagagcc cgaagcttcc agataacagt cttctgataa     1167
ttagagccta cagcagccag aatttgtttt tgttttttgtt tttgtttttt tagctgcttt    1227
taaacctaat ccaaaggttt tgtttaaaac attttgttgc agtgaaaaaa agatatgaag     1287
caatacagta ctcttcaaag aagtccaata aagatgaaaa atatcattag gtattttgag     1347
cacagacgga gatccatgtg ataaaataga ttccttctgc tgggtctgga agtctggaa      1407 accacctgta ggccctggct ttgtcattta ttgactgtat tcagaagata ctatatttgc     1467
tctagagtta actcccattt tagcaagcta gcacaggtga aaattgagtg agttttgat     1527 aacttgtcat ttaaaatcat taatgataat tttcaatgga tctttcagt agccatcacc     1587 agttttgctg ataagacttc ctcacaaccc atttgttgta caaactgttt caaagtagca    1647
atcctttggg ttagtacact tgataccaag tttcattcag ttgattattt tcaaaacaag    1707
gtgatttgtt ttaatgggtt aatgaatact ttgctattac tgttttacaa ttaactttgt   1767
```

```
atatctctgg aaagaggtga atttgtcaat gaaaaaagta ttgtgtagtt cagtgggaaa    1827
aacctgttgt ctgttatagt atcacatcac tttcttacat tgtcatggtt taaattatta    1887
tcttggtgaa atatataggt tagatactta aatgttcata ttattagcac actacaggta    1947
ctacccttaa atcataaata atattaccca ttgtacacag tttccagata tgagttagag    2007
tggctgtgaa gcaactagag gcaaattgtg gcacagagaa tatccagggg aaaattgatt    2067
atgtaagcaa gggctgttct actttgagag agagacagac agactacata atagtaatat    2127
attatataat taatgttata gatacactga acaataaaac attttctgga attatgaatt    2187
aattaacaac ctggatttct gtttccagac ctataaacca tgtaatgaag gactgaaatt    2247
cgtttggcat acactttgtt tctttaaaat tgctagtttc tttctgttat ttttacattt    2307
tcttgtcaga gaatcaaaac tattagtcag tagagttttg tccatgaaat aatatttgga    2367
catttgtgaa ttttccccta tttttttttct tcttttattt atactcaatt ttgaagcact    2427
gtttatgttt gtaggacttt aaacaattag tacttaaagc cccagttaat tttgaacaca    2487
cagagatact tattgtactc tgtgtacagt aagtatttt atgtttacac ttaccagatt    2547
cataaggtta tttgccttta agtgatcttt tgtgatttta cttgattaca gcatgagaag    2607
gtaaaggttg ataaatggga gtaattacat atatatat aatttattat tttttttct    2667
gaagcagagt tttactcttg ttgcccaggc tagagtgcaa tggcacaatc tcggttcact    2727
gcaacctctg cctcccaggt tcaagtgatt ctcctgtctc agcctcccaa gtagctggga    2787
ttacaggtgc ccgccaccat gctcagctaa tttttgtatt tttagtagag acagggttgg    2847
ccaggctggt ctcgagctcc tgacctcagg tgatcctccc acctcggcct cccaaagttc    2907
tgggattaca ggggtgagcc actgtgcccg gccataattt tatattttta gaaaataaag    2967
aatgaaggac aaaagagcac agctaaatga aactgctgct ctaatttatt ccactggaaa    3027
ggtctcagga ctccttaact gttttccagg tttggctctt catatctaac ctgtgctaaa    3087
atgagaaggt atgctaggtg ctgttagaaa tcacaccatt tccaaagaac ccaagtagta    3147
tagagaccaa aatgaggcaa aaataaaaga gatgaaacag gagagtttat ttcttgcata    3207
cttccgacc ttcatcatac aacctctcct aacctccctg tagtctttaa aatgtttaac    3267
ttgcctataa gctaacatgt aataaaacac atactcaatt atatgaatag aagtggagag    3327
ccagaatgct acaaaagaaa tcacagctgc tagaagtatc ctccatagaa acatcaacat    3387
gattgtggat caaatgatt ttcactggat atggaatttg tatgggccat atttattaaa    3447
agagttctgt gtggtcacat agagttcctt tgggatttca tcccactttt caggacttaa    3507
tttgtttggg tttgcttacc taacaagcaa caacaacaac aaaataaata gttccaaaat    3567
ctagtttatt acataaatct ctatgaatcc ttgagggcct atatctatat tataaataaa    3627
tacaaatata gattttttaaa tatctatggg actttgccat ttacagcctt aagtataaaa    3687
ttacgagatt atattctttc cattacccctt tatttctgct aacttttaa agactggaac    3747
attctgtgga tgttgtcaaa gtttgagttt gttttcccct gtgtattata ataaatttgt    3807
ggtattgc                                                              3815
```

<210> SEQ ID NO 15
<211> LENGTH: 281
<212> TYPE: PRT
<213> ORGANISM: Homo sapiens

<400> SEQUENCE: 15

Met Ala Phe Ser Asp Leu Thr Ser Arg Thr Val His Leu Tyr Asp Asn

```
            1               5                  10                 15
Trp Ile Lys Asp Ala Asp Pro Arg Val Glu Asp Trp Leu Leu Met Ser
            20                  25                  30

Ser Pro Leu Pro Gln Thr Ile Leu Leu Gly Phe Tyr Val Tyr Phe Val
            35                  40                  45

Thr Ser Leu Gly Pro Lys Leu Met Glu Asn Arg Lys Pro Phe Glu Leu
            50                  55                  60

Lys Lys Ala Met Ile Thr Tyr Asn Phe Phe Ile Val Leu Phe Ser Val
65                  70                  75                  80

Tyr Met Cys Tyr Glu Phe Val Met Ser Gly Trp Gly Ile Gly Tyr Ser
                    85                  90                  95

Phe Arg Cys Asp Ile Val Asp Tyr Ser Arg Ser Pro Thr Ala Leu Arg
                    100                 105                 110

Met Ala Arg Thr Cys Trp Leu Tyr Tyr Phe Ser Lys Phe Ile Glu Leu
                    115                 120                 125

Leu Asp Thr Ile Phe Phe Val Leu Arg Lys Lys Asn Ser Gln Val Thr
            130                 135                 140

Phe Leu His Val Phe His His Thr Ile Met Pro Trp Thr Trp Trp Phe
145                 150                 155                 160

Gly Val Lys Phe Ala Ala Gly Gly Leu Gly Thr Phe His Ala Leu Leu
                    165                 170                 175

Asn Thr Ala Val His Val Val Met Tyr Ser Tyr Tyr Gly Leu Ser Ala
                    180                 185                 190

Leu Gly Pro Ala Tyr Gln Lys Tyr Leu Trp Trp Lys Lys Tyr Leu Thr
                    195                 200                 205

Ser Leu Gln Leu Val Gln Phe Val Ile Val Ala Ile His Ile Ser Gln
            210                 215                 220

Phe Phe Phe Met Glu Asp Cys Lys Tyr Gln Phe Pro Val Phe Ala Cys
225                 230                 235                 240

Ile Ile Met Ser Tyr Ser Phe Met Phe Pro Leu Leu Phe Leu His Phe
                    245                 250                 255

Trp Tyr Arg Ala Tyr Thr Lys Gly Gln Arg Leu Pro Lys Thr Val Lys
                    260                 265                 270

Asn Gly Thr Cys Lys Asn Lys Asp Asn
                    275                 280
```

<210> SEQ ID NO 16
<211> LENGTH: 18
<212> TYPE: PRT
<213> ORGANISM: Homo sapiens

<400> SEQUENCE: 16

```
Ser Asp Leu Thr Ser Arg Thr Val His Leu Tyr Asp Asn Trp Ile Lys
1               5                   10                  15

Asp Ala
```

<210> SEQ ID NO 17
<211> LENGTH: 19
<212> TYPE: PRT
<213> ORGANISM: Homo sapiens

<400> SEQUENCE: 17

```
Cys His Phe Trp Tyr Arg Ala Tyr Thr Lys Gly Gln Arg Leu Pro Lys
1               5                   10                  15

Thr Val Lys
```

```
<210> SEQ ID NO 18
<211> LENGTH: 66
<212> TYPE: DNA
<213> ORGANISM: Artificial
<220> FEATURE:
<223> OTHER INFORMATION: An artificially synthesized primer for PCR

<400> SEQUENCE: 18
cccctgggat ccaccatggg tcatcatcat caccatcacg aattcgcctt cagtgatctt      60
acatcg                                                                66

<210> SEQ ID NO 19
<211> LENGTH: 36
<212> TYPE: DNA
<213> ORGANISM: Artificial
<220> FEATURE:
<223> OTHER INFORMATION: An artificially synthesized primer for PCR

<400> SEQUENCE: 19
ccgctcgagt caattatctt tgtttttgca agttcc                                36
```